(12) United States Patent
Panandiker et al.

(10) Patent No.: US 11,447,724 B2
(45) Date of Patent: Sep. 20, 2022

(54) COMPOSITIONS THAT INCLUDE SILOXANE COMPOUNDS HAVING PENDANT SILYL ETHER MOIETIES

(71) Applicant: The Procter & Gamble Company, Cincinnati, OH (US)

(72) Inventors: Rajan Keshav Panandiker, West Chester, OH (US); Bernard William Kluesener, Harrison, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 176 days.

(21) Appl. No.: 16/809,596

(22) Filed: Mar. 5, 2020

(65) Prior Publication Data

US 2020/0283706 A1 Sep. 10, 2020

Related U.S. Application Data

(60) Provisional application No. 62/815,511, filed on Mar. 8, 2019.

(51) Int. Cl.
| | | |
|---|---|---|
| *C11D 9/36* | (2006.01) |
| *C11D 3/50* | (2006.01) |
| *C08G 77/14* | (2006.01) |
| *C11D 11/00* | (2006.01) |

(52) U.S. Cl.
CPC .............. *C11D 3/505* (2013.01); *C08G 77/14* (2013.01); *C11D 11/0017* (2013.01)

(58) Field of Classification Search
CPC ........... C11D 3/001; C11D 3/373; C11D 3/50; C11D 3/505; C11D 3/507; C11D 9/44; C11D 11/0017; C11D 3/3738

See application file for complete search history.

(56) References Cited

U.S. PATENT DOCUMENTS

| | | | |
|---|---|---|---|
| 6,046,156 A | 4/2000 | Perry | |
| 6,054,547 A * | 4/2000 | Perry | A61K 8/895 424/65 |
| 6,075,111 A | 6/2000 | Perry | |
| 6,077,923 A | 6/2000 | Perry | |
| 6,153,578 A | 11/2000 | Perry | |
| 7,098,178 B2 | 8/2006 | Gerke | |
| 8,481,776 B2 | 7/2013 | Abe | |
| 10,046,291 B2 | 8/2018 | Yamazaki | |
| 10,590,148 B2 | 3/2020 | Panandiker | |
| 2006/0229230 A1* | 10/2006 | Bauer | A61K 8/891 510/475 |
| 2019/0010293 A1 | 1/2019 | Frankenbach | |
| 2019/0010427 A1 | 1/2019 | Frankenbach | |
| 2019/0024018 A1 | 1/2019 | Panandiker | |
| 2019/0024019 A1* | 1/2019 | Panandiker | C08G 77/56 |
| 2019/0359913 A1 | 11/2019 | Panandiker | |
| 2020/0095267 A1 | 3/2020 | Panandiker | |

FOREIGN PATENT DOCUMENTS

| | | |
|---|---|---|
| EP | 1112273 B1 | 10/2004 |
| EP | 3572449 A1 | 11/2015 |
| GB | 2007703 B | 3/1982 |
| GB | 2319527 B | 5/1998 |
| JP | 2014122288 A | 12/2012 |
| JP | 2014141420 A | 1/2013 |
| WO | WO9628497 A1 | 9/1996 |
| WO | WO2013015293 A1 | 7/2012 |

OTHER PUBLICATIONS

International Search Report; International Application No. PCT/US2020/021071; dated May 29, 2020; 12 pages.
Ganicz, Tomasz, et al.; Organosilicon Fragrance Carriers; Silicon (2015) 7: pp. 333-341; Published online: Aug. 4, 2015.
Perry, Robert J.; GE Silicones; Waterford, New York; "Pro-fragrant" Silicone Delivery Polymers; Delivery System Handbook for Personal Care and Cosmetic Products; Edited by: Rosen, Meyer R.; Section 32; pp. 667-682; Copyright 2005 by William Andrew, Inc.; Norwich, NY; www.williamandrew.com; ISBN: 0-8155-1504-9.

* cited by examiner

*Primary Examiner* — Charles I Boyer
(74) *Attorney, Agent, or Firm* — Gregory S. Darley-Emerson

(57) ABSTRACT

Consumer product compositions that include siloxane compounds having pendant silyl ether moieties, which may include perfume raw material fragments. Such siloxane compounds. Methods related to such compounds and compositions.

20 Claims, 1 Drawing Sheet

| Synthesis Example | Structure | Notes |
|---|---|---|
| 1 | $\text{H}_3\text{C}-\underset{\underset{\text{CH}_3}{|}}{\overset{\overset{\text{CH}_3}{|}}{\text{Si}}}-\text{O}-\left[\underset{\underset{\text{CH}_3}{|}}{\overset{\overset{\text{CH}_3}{|}}{\text{Si}}}-\text{O}\right]_p\left[\underset{\underset{\text{CH}_2\text{CH}_2\text{CH}_2\text{Si}(\text{OR})_3}{|}}{\overset{\overset{\text{CH}_3}{|}}{\text{Si}}}-\text{O}\right]_m\underset{\underset{\text{CH}_3}{|}}{\overset{\overset{\text{CH}_3}{|}}{\text{Si}}}-\text{CH}_3$ | R = geraniol fragment<br>p = about 20<br>m = about 8 |
| 2 | (similar structure with Si(OR)$_2$CH$_3$ pendant) | R = geraniol fragment<br>p = about 20<br>m = about 8 |
| 3 | (similar structure with Si(OR)(CH$_3$)$_2$ pendant) | R = geraniol fragment<br>p = about 20<br>m = about 8 |
| 4 | (similar structure with Si(OR)$_2$CH$_3$ pendant) | R = geraniol fragment<br>p = about 23<br>m = about 5 |
| 5 | (similar structure, propyl linker to Si(OR)$_3$) | R = geraniol fragment<br>p = about 20<br>m = about 8 |
| 6 | (similar structure, propyl linker to Si(OR)$_3$) | R = (E,Z)-2,6-nonadien-1-ol fragment<br>p = about 20<br>m = about 8 |
| 7 | (similar structure with R$_1$ substituent on middle Si) | R = geraniol fragment<br>R$_1$ = CH$_3$ or CH$_3$(CH$_2$)$_7$<br>p = about 20<br>m = about 8 |

COMPOSITIONS THAT INCLUDE SILOXANE COMPOUNDS HAVING PENDANT SILYL ETHER MOIETIES

FIELD OF THE INVENTION

The present disclosure relates to consumer product compositions that include siloxane compounds having pendant silyl ether moieties, which may include perfume raw material fragments. The present disclosure further relates to such siloxane compounds. The present disclosure further relates to methods related to such compounds and compositions.

BACKGROUND OF THE INVENTION

Siloxane compounds may be used as a perfume delivery aid in consumer product compositions. For example, the perfume may be bound to the siloxane compound, which may facilitate deposition onto a target surface. The bond between the perfume moiety and the siloxane compound may then break, releasing the perfume.

However, challenges remain with such delivery systems. For example, the compounds may not be chemically stable, and the bond between the siloxane and the perfume fragment may break (for example, via hydrolysis) prior to deposition. Furthermore, due to mole ratio limitations related to available loading sites on the siloxane compound, it can be challenging to load the siloxane compound with a sufficient amount of perfume to make such a delivery system useful and cost-effective. In conventional siloxanes, loading can be increased by lowering the molecular weight of the siloxane. However, such compounds are difficult to emulsify and lack chemical and physical stability.

There is a need for improved siloxane compounds that can be used as perfume delivery systems, as well as consumer products that include such siloxane compounds.

SUMMARY OF THE INVENTION

The present disclosure relates to consumer product compositions that include siloxane compounds having pendant silyl ether moieties, which may include perfume raw material fragments.

For example, the present disclosure relates to a consumer product composition that includes a siloxane compound and a consumer product adjunct, where the siloxane compound includes a siloxane backbone and at least one pendant group connected to the siloxane backbone, the at least one pendant group including a silyl ether moiety that includes a perfume raw material fragment, the pendant group further including a linker group moiety that links the silyl either moiety to the siloxane backbone, where the siloxane compound is further characterized by at least one of the following: a viscosity of from about about 10 cps to about 60,000 cps, or from about 20 cps to about 30,000 cps, or from about 30 cps to about 10,000 cps, or from about 50 cps to about 5,000 cps, or from about 50 cps to about 3000 cps; and/or a number average molecular weight from about 600 to about 100,000 Daltons, or from about 1000 to about 75,000 Daltons, or from about 1200 to about 50,000 Daltons. The perfume raw material fragment may be derived from, or the residue of, a hydroxyl-containing perfume raw material.

The present disclosure also relates to a consumer product composition that includes a siloxane compound and a consumer product adjunct, where the siloxane compound includes one or more repeat units according to Formula (I), as described in more detail below.

The present disclosure further relates to siloxane compounds as described herein, including such compounds per se.

The present disclosure further relates to a method of treating a surface with a consumer product composition as described herein, where the method may include the step of contacting a surface, preferably a fabric, with the consumer product composition, optionally in the presence of water.

BRIEF DESCRIPTION OF THE DRAWINGS

The FIGURES herein are illustrative in nature and are not intended to be limiting.

FIG. 1 shows the structures of Synthesis Examples 1-7.

DETAILED DESCRIPTION OF THE INVENTION

The present disclosure relates to siloxane compounds that are useful as perfume delivery systems, as well as related consumer product compositions and related processes.

The siloxane compounds of the present disclosure include silyl ether moieties, each of which may provide up to three loading sites per pendant group for the perfume raw materials. Furthermore, the silyl ether moieties are located on pendant portions that connect to or hang from a siloxane backbone; because the siloxane backbone may include multiple pendants, the number of available loading sites is further increased compared to a siloxane compound capable of being loaded only at the terminal ends of the compound.

Additionally, the siloxane compounds of the present disclosure may be characterized by a certain molecular weight. Without wishing to be bound by theory, it is believed that by providing a siloxane compound characterized by a molecular weight above a certain threshold, the stability of the siloxane-based delivery system is improved. For example, siloxane compounds having pendant silyl ether linking groups in certain compositions having a certain pH, for example in an aqueous composition having an acidic pH, may be generally be prone to hydrolysis. However, it is believed that when the siloxane compound is above a certain molecular weight, the hydrophobic siloxane backbone will effectively shield the silyl ether group, thereby inhibiting hydrolysis and improving the perfume delivery efficiency. That being said, compounds of too great a molecular weight may be difficult to process.

Such siloxane compounds, compositions containing the siloxane compounds, and related processes are discussed in more detail below.

As used herein, the articles "a" and "an" when used in a claim, are understood to mean one or more of what is claimed or described. As used herein, the terms "include," "includes," and "including" are meant to be non-limiting. The compositions of the present disclosure can comprise, consist essentially of, or consist of, the components of the present disclosure.

The terms "substantially free of" or "substantially free from" may be used herein. This means that the indicated material is at the very minimum not deliberately added to the composition to form part of it, or, preferably, is not present at analytically detectable levels. It is meant to include compositions whereby the indicated material is present only as an impurity in one of the other materials deliberately included. The indicated material may be present, if at all, at a level of less than 1%, or less than 0.1%, or less than 0.01%, or even 0%, by weight of the composition.

As used herein, the phrase "consumer product composition" may mean a baby care, beauty care, fabric & home care, family care, feminine care, and/or health care products or devices intended to be used or consumed in the form in which it is sold, and not intended for subsequent commercial manufacture or modification. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; shaving products; products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening.

As used herein the phrase "fabric care composition" includes compositions and formulations designed for treating fabric. Such compositions include but are not limited to, laundry cleaning compositions and detergents, fabric softening compositions, fabric enhancing compositions, fabric freshening compositions, laundry prewash, laundry pretreat, laundry additives, spray products, dry cleaning agent or composition, laundry rinse additive, wash additive, post-rinse fabric treatment, ironing aid, unit dose formulation, delayed delivery formulation, detergent contained on or in a porous substrate or nonwoven sheet, and other suitable forms that may be apparent to one skilled in the art in view of the teachings herein. Such compositions may be used as a pre-laundering treatment, a post-laundering treatment, or may be added during the rinse or wash cycle of the laundering operation.

Unless otherwise noted, all component or composition levels are in reference to the active portion of that component or composition, and are exclusive of impurities, for example, residual solvents or by-products, which may be present in commercially available sources of such components or compositions.

All temperatures herein are in degrees Celsius (° C.) unless otherwise indicated. Unless otherwise specified, all measurements herein are conducted at 20° C. and under the atmospheric pressure.

In all embodiments of the present disclosure, all percentages are by weight of the total composition, unless specifically stated otherwise. All ratios are weight ratios, unless specifically stated otherwise.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Consumer Product Compositions

The present disclosure relates to consumer product compositions. The consumer product compositions may comprise a siloxane compound of the present disclosure and a consumer product adjunct. The present disclosure also relates to compositions that comprise a siloxane compound of the present and a carrier.

The consumer product compositions may be useful for delivering a perfume to a target surface. As described above, it is believed that the siloxane compound facilitates deposition, and then the perfume raw material is released, for example when the bond of the silyl ether is broken (e.g., via hydrolysis).

The consumer product compositions of the present disclosure may be useful as a baby care, beauty care, fabric care, home care, family care, feminine care, and/or health care product or device. The consumer product composition may be a beauty care composition, a fabric care composition, a home care composition, or combinations thereof, preferably a fabric care composition.

The consumer product composition may be a beauty care composition, such as a hair treatment product (including shampoo and/or conditioner), a skin care product (including a cream, lotion, or other topically applied product for consumer use), a shave care product (including a shaving lotion, foam, or pre- or post-shave treatment), personal cleansing product (including a liquid body wash, a liquid hand soap, and/or a bar soap), a deodorant and/or antiperspirant, or mixtures thereof. The composition may be a hair treatment product, preferably a conditioner. The consumer product composition may be a home care composition, such as an air care, car care, dishwashing, hard surface cleaning and/or treatment, and other cleaning for consumer or institutional use.

The consumer product composition may be a fabric care composition, such as a laundry detergent composition (including a heavy-duty washing detergent), a fabric conditioning composition (including a fabric softening and/or enhancing composition), a laundry and rinse additive, a fabric pre-treatment composition, a fabric refresher composition, or a mixture thereof.

The fabric care composition may be a fabric conditioning composition. Such compositions may provide softness, conditioning, and/or freshness benefits to fabrics. The compositions may be intended to treat fabrics through the wash cycle and/or the rinse cycle of an automatic washing machine, preferably the rinse cycle. The fabric care composition may include less than 5%, or less than 2%, or less than 1%, or less than about 0.1%, by weight of the composition, of anionic surfactant, or even be substantially free of anionic surfactant.

The consumer product composition, preferably fabric care compositions, of the present disclosure may be in any suitable form. The composition may be in the form of a liquid composition (including a sprayable liquid composition), a granular composition, a single-compartment pouch, a multi-compartment pouch, a dissolvable sheet, a (water-soluble) pastille or bead, a fibrous article (which may be water-soluble or water-dispersible, or substantially non-soluble/non-dispersible), a tablet, a bar, a flake, a foam/mousse, a non-woven sheet (e.g., a dryer sheet), or a mixture thereof. The composition can be selected from a liquid, solid, or combination thereof. The composition may be in the form of a liquid fabric conditioner, a sprayable liquid composition, a foam/mousse, a dryer sheet, or a (water-soluble) pastille/bead.

The compositions of the present disclosure may have a pH of from about 2 to about 12, or from about 2 to about 8.5, or from about 2 to about 7, or from about 2 to about 5. The compositions of the present disclosure may have a pH of from about 2 to about 4, preferably a pH of from about 2 to about 3.7, more preferably a pH from about 2 to about 3.5, preferably in the form of an aqueous liquid. It is believed that such pH levels facilitate stability of the siloxane polymer. The pH of a composition is determined by dissolving/dispersing the composition in deionized water to form a solution at 10% concentration, at about 20° C.

The composition may include a carrier. Suitable carriers may include be liquid carriers or solid carriers. Suitable carriers may include water, non-aqueous solvents, a salt, or a combination thereof.

The composition may include water. The composition may be aqueous. The composition, which may be a liquid composition, may comprise at least 50% by weight of water, preferably at least 75%, or even more than 85% by weight of water. The composition may comprise from about 50% to about 99%, or from about 60% to about 98%, or from about 75% to about 98%, or from about 80% to about 98%, or from about 85% to about 98%, or from about 90% to about 98%, by weight of the composition, of water. The composition may comprise from about 10% to about 90%, by weight of the composition, of water, preferably from about 25% to about 80%, more preferably from about 45% to about 70%. The siloxane polymers of the present disclosure are believed to be particularly well-suited to aqueous compositions, as the hydrophobic backbone of the siloxane polymer facilitates stability benefits of the silyl ether moieties.

Non-aqueous solvents may include organic solvents, such as methanol, ethanol, propanol, isopropanol, 1,3-propanediol, 1,2-propanediol, ethylene glycol, glycerine, glycol ethers, hydrocarbons, or mixtures thereof. Other non-aqueous solvents may include lipophilic fluids such as siloxanes or other silicones, hydrocarbons, perfluorinated amines, perfluorinated and hydrofluoroether solvents, or mixtures thereof. Amine-containing solvents, such as monoethanolamine, diethanolamine and triethanolamine, may also be used.

The carrier may be a water-soluble carrier. Such carriers may include water-soluble inorganic alkali metal salt, water-soluble alkaline earth metal salt, water-soluble organic alkali metal salt, water-soluble organic alkaline earth metal salt, water soluble carbohydrate, water-soluble silicate, water-soluble urea, and any combination thereof. Polyalkylene glycols, such as polyethlyene glycols, may be suitable carriers, particularly if the composition is in solid form, such as a bead or pastille.

Siloxane Compounds

The present disclosure relates to certain siloxane compounds. As used herein, "siloxane compound" and "siloxane polymer" may be used interchangeably, unless otherwise indicated.

The siloxane compounds of the present disclosure may be stand-alone compounds, or in a premix or feedstock composition, or in a consumer product composition, or in an end-use composition that is not a consumer product. Preferably, the siloxane compound is present in a consumer product composition, which may have widespread applicability and/or availability. Suitable consumer product compositions are described in more detail above.

A consumer product of the present disclosure may comprise from about 0.1% to about 20%, preferably from about 0.1% to about 10%, more preferably from about 0.1% to about 5%, or from about 0.1% to about 3%, or from about 0.1% to about 1%, by weight of the consumer product composition, of the siloxane compound.

The siloxane compound may comprise a siloxane backbone and at least one pendant group connected to the siloxane backbone. The at least one pendant group may comprise a silyl ether moiety, where the silyl ether moiety comprises a perfume raw material fragment. The pendant group may comprise a linker group moiety that links the silyl either moiety to the siloxane backbone. The siloxane compound may comprise from about 1 to about 1400 pendant groups, each of which is connected to and/or hangs off of the siloxane backbone. It is believed that, for example, providing a pendant group that includes a linker group moiety makes the synthesis of such molecules relatively easier than connecting a perfume raw material residue directly to the siloxane backbone.

The siloxane compound may be characterized by a number average molecular weight from about 600 to about 100,000 Daltons, or from about 1000 to about 75,000 Daltons, or from about 1200 to about 50,000 Daltons.

The siloxane compound may be characterized by a viscosity of from about about 10 cps to about 60,000 cps, or from about 20 cps to about 30,000 cps, or from about 30 cps to about 10,000 cps, or from about 50 cps to about 5,000 cps, or from about 50 cps to about 3000 cps. Viscosity can serve as a proxy for size of the siloxane compound and typically a certain minimum size is desirable for improved stability.

Viscosity of the parent silicone compound (e.g., a silicone hydride) before attachment of the perfume raw material fragment may be from about 10 cps to about 60,000 cps, or from about 20 cps to about 30,000 cps, or from about 30 cps to about 10,000 cps, or from about 50 cps to about 5,000 cps, or from about 50 cps to about 3000 cps. It is understood that the viscosity and the molecular weight of the claimed siloxane compound will depend on the molecular weight of the pendant group, such as the pendant alcohol.

As noted above, it is believed that siloxane compounds above a certain molecular weight or size facilitate stability of the delivery system, for example by protecting the silyl ether moiety and/or perfume raw material fragments from the environment, particularly aqueous environments, and/or by inhibiting hydrolysis. Suitable siloxane compounds and/or siloxane backbones are described in more detail below.

The silyl ether moiety comprising a perfume raw material fragment may be derived from a residue formed upon the reaction of, for example, a silyl ether, a silanol group (Si—OH) or a chlorosilane group (Si—Cl) with a hydroxyl group in a perfume raw material. It is useful for the perfume raw material to contain a hydroxyl group so as to form a convenient reaction with silanol group, or a chlorosilane group or exchange with a silyl ether group.

Such silyl ether moieties comprising a perfume raw material fragment can also be produced by reacting epoxy containing silyl ethers, silanol, chlorosilane groups with a hydroxyl group in a perfume raw material and then reacting such compounds with a nucleophilic group attached to a siloxane backbone. Preferred nucleophilic groups include amino and carbinol.

The silyl ether moieties comprising a perfume raw material fragment can also be produced by reacting compounds containing silyl ethers, silanol, or chlorosilane groups with a hydroxyl group in a perfume raw material, and which that compound also contains functional groups capable of reacting with a siloxane hydride or other functionalized siloxane backbone.

The silyl ether moiety may comprise at least one perfume raw material fragments, or at least two perfume raw material fragments, preferably three perfume raw material fragments. Such configurations are useful for delivering greater loads of perfume raw materials.

The perfume raw material from which the fragment is derived may be characterized by a molecular weight of about 30 Da to about 500 Da and/or a CLogP from about −2.0 and to about 8.0; preferably a CLogP from about −2.0 and to about 7.0; more preferably a CLogP from about −2.0 and to about 5.0. It is believed that such materials are able to be conveniently released from the siloxane compound.

The perfume raw material fragment may be derived from a hydroxyl-containing perfume raw material. The perfume raw material fragment may be derived from a perfume raw material comprising an aliphatic alcohol or aromatic alcohol. Preferably, the perfume raw material is a hydroxyl-containing perfume raw material. It is believed that such siloxane compounds are particularly suited as a perfume delivery system, as the siloxane component helps to deliver the perfume to relevant target surfaces such as fabrics. Suitable perfume raw materials and fragments thereof are described in more detail below.

The siloxane compound may comprise one or more repeat units according to Formula (I):

Formula (I)

wherein:

each $R_1$ is independently selected from the group consisting of H, OH, $C_1$-$C_{32}$ alkyl, $C_1$-$C_{32}$ substituted alkyl, $C_6$-$C_{32}$ aryl, $C_5$-$C_{32}$ substituted aryl, $C_6$-$C_{32}$ alkylaryl, $C_6$-$C_{32}$ substituted alkylaryl, $C_1$-$C_{32}$ alkoxy and $C_1$-$C_{32}$ substituted alkoxy; preferably each $R_1$ is independently selected from the group consisting of H, OH, $C_1$-$C_{16}$ alkyl, $C_1$-$C_4$ alkoxy, more preferably each $R_1$ is independently selected from the group consisting of H, OH, methyl, methoxy, and ethoxy;

each L is a linking bivalent alkylene radical, preferably each L is independently selected from the group consisting of —$(CH_2)_s$—; —$(H_2C)_sOC_6H_4$—;

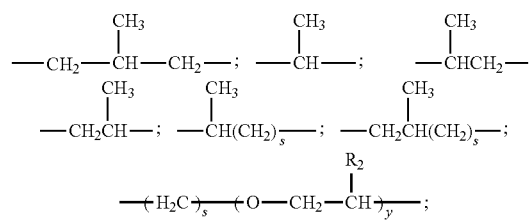

and combinations thereof;

wherein each $R_2$ is independently selected from the group consisting of H, $C_1$-$C_4$ alkyl, substituted alkyl, aryl, substituted aryl, and combinations thereof, preferably H or $C_1$-$C_4$ alkyl, most preferably H or methyl;

each s is independently an integer of from 1 to about 20, preferably each s is independently an integer of from 2 to about 12;

each y is independently an integer of from 1 to about 100, preferably each y is independently an integer of from 1 to about 20, more preferably y is independently an integer of from 1 to about 10;

each Z is selected from the group consisting of:

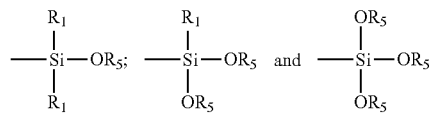

or mixtures thereof, wherein each $R_1$, if present, is independently selected from the group as provided above, and wherein each $R_5$ is independently selected from the group consisting of H, $C_1$-$C_{32}$ alkyl, $C_1$-$C_{32}$ substituted alkyl, $C_6$-$C_{32}$ aryl, $C_5$-$C_{32}$ substituted aryl, $C_6$-$C_{32}$ alkylaryl, and $C_6$-$C_{32}$ substituted alkylaryl, wherein at least one $R_5$ in the siloxane compound is the residue of a hydroxyl-group-containing perfume raw material;

wherein index m is an integer of from about 1 to about 500, preferably from about 5 to about 500, or from about 5 to 200, or from about 5 to 100; index m may be from about 10 to about 500, preferably m is an integer from about 10 to about 200, more preferably m is an integer from about 10 to about 100.

For clarity, the -L-Z group of the repeat units according to Formula (I) represents the pendant group(s) of the siloxane compound, and at least the $R_5$ group represents a perfume raw material fragment. The at least one $R_5$ in the siloxane compound that is the residue of (and/or derived from) a hydroxyl-group-containing perfume raw material may, for example, be formed upon the reaction (e.g., a condensation reaction) of a silanol group, a chlorosilane, or silyl ether with a hydroxyl group of a hydroxyl-group-containing perfume raw material.

Preferably, L is —$(CH_2)_s$—, wherein each s is independently an integer of from 1 to about 20, preferably each s is independently an integer of from 2 to about 12.

In order to assure a suitable molecular weight, particularly in aqueous compositions characterized by an acidic pH, for example a pH of from about 2 to about 5, it may be that the sum of p+m is from about 20 to about 1000, preferably from about 20 to about about 200.

The siloxane compounds of the present disclosure may further comprise one or more repeat units according to Formula (II):

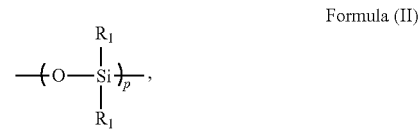

Formula (II)

wherein each $R_1$ is independently selected from the group as described above, and wherein index p is an integer of from about 0 to about 500, preferably p is an integer from about 5 to about 400, more preferably p is an integer from about 5 to about 200.

It is understood that the groups according to Formula (I) and the groups according to Formula (II), when both present, are preferably randomly distributed in the molecule.

In order to assure a suitable molecular weight, particularly in aqueous compositions characterized by an acidic pH, for example a pH of from about 2 to about 5, it may be that the sum of p+m is from about 20 to about 1000, preferably from about 20 to about about 200.

The ratio of index p to index m (p:m) may be from about 10:1 to about 1:10, preferably from about 5:1 to about 1:4, more preferably from about 3:1 to about 1:3. A relatively higher value of m may be desired because the higher the value of m, the more pendant groups will be present, thereby enabling relatively higher loading capacities of the perfume raw material fragments. That being said, some incorporation of the groups according to Formula (II) may be desired to give sufficient spacing of the groups according to Formula (I) to allow for better reactivity of the pendant group with the siloxane backbone.

The repeat units according to Formula (I) may comprise repeat units according to Formula (III):

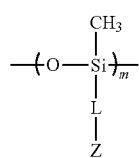

Formula (III)

wherein L, Z, and m are as described above and/or below.

The repeat units according to Formula (II) may comprise repeat units according to Formula (IV):

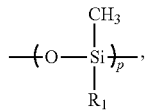

Formula (IV)

wherein $R_1$ and p are as described above and/or below.

As the ratio of p:m is decreased, it may be desirable to use multiple types of $R_1$ groups to drive the reaction to completion. As such, the repeat units according to Formula (I), $R_1$ may be independently selected from $C_1$-$C_{32}$ alkyl groups, preferably independently selected from methyl ($C_1$) groups and $C_2$-$C_{18}$ alkyl groups, more preferably a combination thereof. For clarity, such siloxane polymers may have empirical structures as shown in Formula (V):

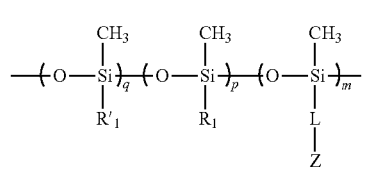

Formula (V)

wherein $R_1$ is a methyl (C1) group, $R'_1$ is selected from $C_2$-$C_{18}$ alkyl groups, q is an integer from 1 to 20; the ratio of q:(m+p) may be less than 1:10, preferably less than 1:20.

The siloxane compound may comprise repeat units according to Formula (I) and/or Formula (III), wherein at least one Z moiety, or wherein all the Z moieties, is/are selected from the group consisting of:

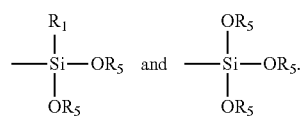

The siloxane compound may comprise repeat units according to Formula (I) and/or Formula (III), wherein at least one Z moiety, or wherein all the Z moieties, is/are

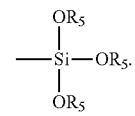

As described above, at least one $R_5$ group in the siloxane compound, preferably at least one $R_5$ group in each pendant of the siloxane compound, more preferably all the $R_5$ groups in each pendant and/or the siloxane compound, may be the residue resulting from the removal of one —OH group from a hydroxyl-group-containing perfume raw material. The hydroxyl-group-containing perfume raw material may be an aliphatic alcohol or an aromatic alcohol, preferably an aliphatic alcohol. The hydroxyl-group-containing perfume raw material may more preferably be a hydroxyl-containing perfume raw material.

The hydroxyl-containing perfume raw material resulting in the $R_5$ group may be selected from the group consisting of a perfume raw material ("PRM") selected from Table A as provided below.

TABLE A

| PRM chemical name(s) | Commercial/common name(s) |
| --- | --- |
| 3,7,11-Trimethyl-2,6,10-dodecatrien-12-ol; 2,6,10-Dodecatrien-1-ol, 3,7,11-trimethyl-; Farnesyl alcohol; 3,7,11-Trimethyl-2,6,10-dodecatrien-1-ol; 3,7,11-Trimethyl-2,6,10-dodecatrienol; Trimethyl-2,6,10-dodecatriene-1-ol; (2E,6E)-3,7,11-Trimethyl-2,6,10-dodecatrien-1-ol; α-Farnesol; alpha-Farnesol; 3,7,11-Trimethyldodeca-2,6,10-trien-1-ol; 3,7,11-Trimethyl-2,6,10-dodecatrien-1-ol (farnesol); (E)-alpha-Farnesol | Farnesol |
| (1-Methyl-2-(1,2,2-trimethylbicyclo[3.1.0]-hex-3-ylmethyl)cyclopropyl)methanol (Mixture of diastereoisomers) | Javanol ® |
| 2-Methyl-3-{(1,7,7-trimethylbicyclo{2.2.1}hept-2-yl)oxy}exo-1-propanol and isomers | Bornafix ® |
| 2-Methyl-4-(2,2,3-trimethylcyclopent-3-en-1-yl)butan-1-ol; 2-Methyl-4-(2,2,3-trimethyl-3-cyclopenten-1-yl)-butan-1-ol | Brahmanol ® |

TABLE A-continued

| PRM chemical name(s) | Commercial/common name(s) |
| --- | --- |
| 2-Ethyl-4-(2,2,3-trimethyl-3-cyclo-penten-1-yl)-2-buten-1-ol; 2-Ethyl-4-(2,2,3-trimethyl-3-cyclopenten-1-yl)-2-buten-1-ol; B-Ethyl-2,2,3-trimethyl-3-Cyclopentene-1-but-2-enol; Ethyl Trimethylcyclopentene Butenol | Bacdanol ® Bacdanol ; Sandranol; Bangalol; Sandolen ; Balinol; Laevo Trisandol; Levosandol; Mayol ® 957230 |
| Cyclohexanemethanol, 4-(1-methylethyl)-, cis-; 4-Isopropylcyclohexanemethanol; | |
| 2-Methyl-5-phenylpentan-1-ol | Rosaphen ® |
| 3-Methyl-5-phenylpentanol; 3-Methyl-5-phenyl-1-pentanol; | Phenoxanol ®; Mefrosol; Phenyl hexanol |
| 9-decen-1-ol; 9-Decenol; | Rosalva; Trepanol |
| 2-Methyl-4-(2,2,3-trimethyl-3-cyclopenten-1-yl)-2-buten-1-ol;; 2-Buten-1-ol, 2-methyl-4-(2,2,3-trimethyl-3-cyclopenten-1-yl)-; 2-Buten-1-ol, 2-methyl-4-(2,2,3-trimethyl-3-cyclopenten-1-yl)- | Hindinol; Sandalmysore core; Santalaire; Madranol; Santaliff ™ |
| 3-Cyclohexene-1-propanol gamma 4-dimethyl- | Cyclomethylene citronellol 937001 |
| 2,2-Dimethyl-3-(3-methylphenyl)propan-1-ol | Majantol ® |
| 3,7-Dimethyl-6-octen-1-ol, (-)-Citronellol; Rhodinol | Citronellol |
| (2E,6Z)-nona-2,6-dien-1-ol | 2 6 Nonadienol |
| 2-[(1,7,7-Trimethylbicyclo[2.2.1]hept-2-yl)oxy]-ethanol | Cedanol |
| 2,4,6-Trimethyl-3-cyclohexene-1-methanol | Isocyclogeraniol |
| 3,7-Dimethyl-trans-2,6-octadien-1-ol; 3,7-Dimethyl-2,6-octadien-1-ol (isomers); trans-Geraniol; Guaniol; Lemonol; trans-3,7-Dimethyl-2,6-octadien-1-ol; Geraniol alcohol; Geraniol extra; Geranyl alcohol; 2,6-Dimethyl-trans-2,6-octadien-8-ol; 2,6-Octadien-1-ol, 3,7-dimethyl-, trans-; 3,7-Dimethyl-trans-2,6-octadien-1-ol; (E)-3,7-Dimethyl-2,6-octadien-1-ol; Meranol; trans-3,7-Dimethyl octa-2,6-dien-1-ol; (2E)-3,7-Dimethyl-2,6-octadien-1-ol; Nerol; Neryl alcohol; trans-3,7-Dimethyl-2,6-octadien-1-ol (geraniol); t-Geraniol; (E)-Geraniol; (E)-3,7-Dimethyl-2,6-octadien-1-ol; Geraniol (E) | Geraniol |
| Dihydrocinnamic alcohol; 3-Phenylpropanol; Benzenepropanol; 1-Propanol, 3-phenyl-; γ-Phenylpropanol; γ-Phenylpropyl alcohol; (3-Hydroxypropyl)benzene;Hydrocinnamic alcohol; Hydrocinnamyl alcohol; 3-Phenyl-n-propanol; 3-Phenyl-1-propanol; 3-Phenylpropyl alcohol; 3-Benzenepropanol; Phenylpropyl alcohol; 1-Hydroxy-3-phenylpropane; 3-Phenylpropan-1-ol; Phenylpropylic alcohol | 3-Phenylpropyl alcohol |
| Cinnamic alcohol; 3-Phenyl-2-propen-1-ol; Cinnamyl alcohol; γ-Phenylallyl alcohol; Phenyl-2-propen-1-ol; Styrone; Styryl carbinol; 3-Phenylallyl alcohol; 1-Phenyl-1-propen-3-ol; 3-Phenyl-2-propen-1-ol; 3-Phenyl-2-propenol; Alkohol skoricovy; 3-Fenyl-2-propen-1-ol; Peruvin; Phenyl-2-propenol; Phenylallyl alcohol; (2E)-3-Phenyl-2-propen-1-ol; 3-phenylprop-2-en-1-ol; 2-Propen-1-ol, 3-phenyl- | Cinnamic alcohol |
| 2-Hexen-1-ol, (E)-; trans-2-Hexen-1-ol; trans-2-Hexenol; 2-Hexenol; 2-Hexen-1-ol, trans-; (2E)-2-Hexen-1-ol; (E)-2-Hexenol; (E)-Hex-2-en- 1-ol; (E)-Hex-2-enol; (E)-2-Hexene-1-ol; Hex-2(E)-enol; t-2-Hexen-1-ol; 2-(E)-hexenol; trans-Hex-2-en-1-ol | trans-2-Hexenol |
| 4-(5,5,6-Trimethylbicyclo[2.2.1]hept-2-yl)cyclohexan-1-ol (and isomers, 85% solution in IPM) | Sandela ® |
| 1-Naphthalenol,1,2,3,4,4a,5,8,8a-octahydro-2,2,6,8-tetramethyl- | Octalynol 967544 |
| 3-Methyl-5-(2,2,3-trimethyl-3-cyclopenten-1-yl)-4-penten-2-ol; | Ebanol |
| 4-Methyl-3-decen-5-ol | Undecavertol |
| 4-Penten-2-ol, 3,3-dimethyl-5-(2,2,3-trimethyl-3-cyclopenten-1-yl)-; | Nirvanol ® 974650; Polysantol ® 974656 |
| 3-Methyl-4-phenylbutan-2-ol | Muguesia |
| 2-Methoxy-4-allylphenol | Eugenol |
| Cyclohexanepropanol, 2,2,6-trimethyl-alpha-propyl-; 1-(2,2,6-Trimethylcyclohexyl)hexan-3-ol | Norlimbanol 967412; Timberol ®; |
| 5-Propenyl-2-ethoxyphenol; | Propenyl guaethol; Vanitrope |

TABLE A-continued

| PRM chemical name(s) | Commercial/common name(s) |
| --- | --- |
| 1-(4-Isopropyl-cyclohexyl) ethanol; 1-(4-Isopropylcyclohexyl)-ethanol | Mugetanol |
| 2-Pentylcyclopentan-1-ol; 2-Pentylcyclopentanol | Cyclopentol HC 937165 |
| 3,7,11-Trimethyl-1,6,10-dodecatrien-3-ol | Nerolidol |
| Cedrol Crude | Cedrol |
| 3,7-Dimethyl-7-hydroxyoctan-1-al dimethyl acetal | Hydroxycitronellal dimethyl acetal |
| 4-Methyl-2-(2-methylpropyl)tetrahydro-2H-pyran-4-ol; Florol ® 966458 | Florosa |
| 2,5,5-Trimethyl-octahydronaphthalen-2-ol; 2,5,5-Trimethyl-1,2,3,4,4α,5,6,7-octahydro-2-naphthalenol; | Ambrinol 20-T Ambrinol; Ambrinol S |
| 4-Methyl-1-isopropyl-3-cyclohexen-1-ol | Terpinen-4-ol |
| 3,7-Dimethyl-1,6-nonadien-3-ol (cis & trans) | Ethyl linalool |
| 1-Methyl-3-(2-methylpropyl)cyclohexanol | Rossitol ® |
| 4-Phenyl-2-methyl-2-butanol | α,α-Dimethylphenyl-ethylcarbinol |
| 3,7-Dimethyloctan-1,7-diol | Hydroxyol |
| 1-Methyl-4-isopropylcyclohexane-8-ol | Dihydro terpineol |
| 3,7-Dimethyl-1,6-octadiene-3-ol | Linalool |
| 3,7-Dimethyl-4,6-octadien-3-ol | Allo-Ocimenol; Muguol |
| 2-(4-Methyl-cyclohex-3-enyl)-propan-2-ol; p-Menthan-8-ol | alpha Terpineol, Lindenol ™ |
| 1-Phenyl-2-methyl-2-propanol; α,α-Dimethylbenzyl carbinol; benzeneethanol, α,α-dimethyl- | 2-methyl-1-phenylpropan-2-ol |
| Cyclohexanepropanol,2,2-dimethyl- | Coranol 928130 |
| 2,6-Dimethyl-7-octen-2-ol; 2-Methyl-6-methyleneoct-7-en-2-ol, dihydro derivative; 7-Octen-2-ol, 2,6-dimethyl-; 2,6-Dimethyl-7-octen-2-ol; 3,7-Dimethyl-1-octen-7-ol; 2,6-Dimethyl-oct-7-en-2-ol; Mircenol, 6,10-dihydro | Dihydromyrcenol, Dihydro Myrcenol |
| 3,7-Dimethyloctan-3-ol | Tetrahydrolinalool |
| 2,6-Dimethyl-2-octanol | Tetrahydro myrcenol |
| 2,6-Dimethyl-2-heptanol | Dimetol, Freesiol, Lolitol |
| 2-Hexen-1-ol | Beta Gamma Hexenol |
| 3-Hexen-1-ol | Beta Gamma Hexenol |
| Ethanol, 2,2'-oxybis- | Calone 161 |
| Benzoic acid, 2-amino-, methyl ester | Methyl Anthranilate |
| 4,7-Methano-1H-inden-6-ol, 3a,4,5,6,7,7a-hexahydro-, acetate | Flor Acetate |
| 2(3H)-Furanone, 5-ethyldihydro- | Gamma Hexalactone |
| Phenol, 4-methyl- | Para Cresol |
| 2H-Pyran, 3,6-dihydro-4-methyl-2-(2-methyl-1-propenyl)- | Nerol Oxide |
| Benzeneethanol, .beta.-methyl- | Hydratropic Alcohol |
| Benzeneethanol, .alpha., .alpha.-dimethyl- | Dimethyl Benzyl Carbinol |
| Benzoic acid, 2-(methylamino)-, methyl ester | Dimethyl Anthranilate |
| 4H-Pyran-4-one, 2-ethyl-3-hydroxy- | Ethyl Maltol |
| 1-Heptanol | Heptyl Alcohol |
| Ethanol, 2-(2-methoxyethoxy)- | Veramoss Sps |
| Cyclohexaneethanol | Cyclohexyl Ethyl Alcohol |
| 4-Hydroxy-3-methoxybenzaldehyde | Vanillin |
| 3-Ethoxy-4-hydroxybenzaldehyde | Ethyl Vanillin |

Preferably, the at least one $R_5$ moiety comprises a perfume raw material fragment derived from hydroxyl-containing perfume raw materials selected from geraniol, 2,6-nonadienol, cinnamic alcohol, linalool, flor acetate, derivatives thereof, or mixtures thereof, as these materials are particularly desired by formulators and/or consumers.

It is contemplated that a single siloxane compound, or even a single pendant, may include perfume raw material fragments (e.g., $R_5$ moieties) of different identities. For example, a single siloxane compound and/or a single pendant may contain both geraniol fragments and nonadienol (e.g., (E,Z)-2,6-nonadien-1-ol) fragments.

Exemplary siloxane compounds that may be useful according to the present disclosure may include any of Synthesis Examples 1-7, or mixtures thereof, as described below.

It is contemplated that a single siloxane compound, or even a single pendant, may include perfume raw material fragments (e.g., $R_5$ moieties) of different identities. For example, a single siloxane compound and/or a single pendant may contain both geraniol fragments and nondianol fragments.

The compositions of the present disclosure may comprise one or more of the hydroxyl-group-containing PRMs provided above that are not bound to a siloxane compound according to the present disclosure (e.g., PRMs in neat/free form, and/or encapsulated PRMs). The free PRM(s) may be the result of hydrolysis of the siloxane compound, and/or the PRMs may be added separately to the composition as neat, premixed, or encapsulated perfumes.

To obtain a siloxane compound according to the present disclosure, a silane containing 1) a functional group(s) capable of reacting with the hydroxyl group of a perfume raw material, such as alkoxysilane or chlorosilane, and 2) a functional group containing a terminal olefin group, such as vinylsilane or allyl silane, is reacted with the hydroxyl group of a perfume raw material to form a silyl ether bond between the silane and the perfume raw material. This intermediate is hydrosilylated to a trimethylsiloxy terminated methylhydrosiloxane-dimethylsiloxane copolymer to yield the silyl-ether-containing siloxane compound.

Alternatively, a silane containing 1) a functional group(s) capable of reacting with the hydroxyl group of a perfume raw material, and 2) a functional group containing a terminal olefin group, can first be reacted with a trimethylsiloxy terminated methylhydrosiloxane-dimethylsiloxane copolymer via hydrosilylation, to yield the intermediate, containing a silane containing a functional group(s) capable of reacting with the hydroxyl group of a perfume raw material. This intermediate is then reacted with the hydroxyl group of a perfume raw material to form a silyl ether bond between the silane and the perfume raw material, yielding the silyl-ether-containing siloxane compound.

During usage of the siloxane compound and/or compositions containing such compounds, it is believed that the silyl ether bond can break, for example via hydrolysis, thereby releasing the hydroxyl-containing perfume raw material, such as a hydroxyl-containing perfume raw material.

Consumer Product Adjuncts

The disclosed compositions may include additional adjunct consumer product adjuncts, which may include: bleach activators, surfactants, delivery enhancing agents, builders, chelating agents, dye transfer inhibiting agents, dispersants, enzymes, enzyme stabilizers, catalytic metal complexes, polymeric dispersing agents, clay and soil removal/anti-redeposition agents, brighteners, suds suppressors, dyes, additional perfumes and/or perfume delivery systems, structure elasticizing agents, fabric conditioning actives (FCAs), anionic surfactant scavengers, carriers, hydrotropes, processing aids, structurants, anti-agglomeration agents, coatings, formaldehyde scavengers, deposition aids, emulsifiers, pigments, or mixtures thereof. The compositions of the present disclosure may be substantially free of one or more of the listed adjuncts materials. The precise nature of these additional components, and levels of incorporation thereof (or even lack thereof), will depend on the physical form of the composition and the nature of the operation for which it is to be used.

The composition may include: from about 0.01% to about 50% of a fabric conditioning active; from about 0.001% to about 15% of an anionic surfactant scavenger; from about 0.01% to about 10%, of a delivery enhancing agent; from about 0.005% to about 30% of a perfume; from about 0.005% to about 30% of a perfume delivery system; from about 0.01% to about 20% of a soil dispersing polymer; from about 0.001% to about 10% of a brightener; from about 0.0001% to about 10% of a hueing dye; from about 0.0001% to about 10% of a dye transfer inhibiting agent; from about 0.01% to about 10% of an enzyme; from about 0.01% to about 20% of a structurant; from about 0.1% to about 80% of a builder; from about 0.1% to about 99% of a carrier; and/or mixtures thereof.

The fabric treatment compositions of the present disclosure may include a fabric conditioning active (FCA). The FCA may be present at a level of from about 1% to about 99%, by weight of the composition. The fabric treatment composition may include from about 1%, or from about 2%, or from about 3%, to about 99%, or to about 75%, or to about 50%, or to about 40%, or to about 30%, or to about 25%, or to about 20%, or to about 15%, or to about 10%, by weight of the composition, of FCA. The fabric treatment composition may include from about 5% to about 30%, by weight of the composition, of FCA.

Fabric conditioning actives (FCAs) suitable for compositions of the present disclosure may include quaternary ammonium ester compounds, silicones, non-ester quaternary ammonium compounds, amines, fatty esters, sucrose esters, silicones, dispersible polyolefins, polysaccharides, fatty acids, softening or conditioning oils, polymer latexes, or combinations thereof.

The composition may include a quaternary ammonium ester compound, a silicone, or combinations thereof, preferably a combination. The combined total amount of quaternary ammonium ester compound and silicone may be from about 5% to about 70%, or from about 6% to about 50%, or from about 7% to about 40%, or from about 10% to about 30%, or from about 15% to about 25%, by weight of the composition. The composition may include a quaternary ammonium ester compound and silicone in a weight ratio of from about 1:10 to about 10:1, or from about 1:5 to about 5:1, or from about 1:3 to about 1:3, or from about 1:2 to about 2:1, or about 1:1.5 to about 1.5:1, or about 1:1.

The composition may contain mixtures of different types of FCAs. The compositions of the present disclosure may contain a certain FCA but be substantially free of others. For example, the composition may be free of quaternary ammonium ester compounds, silicones, or both. The composition may comprise quaternary ammonium ester compounds but be substantially free of silicone. The composition may comprise silicone but be substantially free of quaternary ammonium ester compounds.

The composition may include perfume and/or a perfume delivery system, in addition to the siloxane compounds described above. Suitable perfume delivery systems may include a Polymer Assisted Delivery (PAD) system, Molecule-Assisted Delivery (MAD) system, Cyclodextrin (CD) system, Starch Encapsulated Accord (SEA) system, Zeolite & Inorganic Carrier (ZIC) system, or mixtures thereof. A PAD system may include a resevoir system that includes perfume. Such a system may include a perfume delivery particle that may comprise a shell material and a core material, said shell material encapsulating said core material, which may include perfume. The shell may comprise material selected from the group consisting of polyethylenes; polyamides; polystyrenes; polyisoprenes; polycarbonates; polyesters; polyacrylates; aminoplasts, such as a polyurea (including polyoxymethyleneurea and/or melamine formaldehyde), polyurethane, and/or polyureaurethane; polyolefins; polysaccharide (e.g., alginate and/or chitosan); gelatin; shellac; epoxy resins; vinyl polymers; water insoluble inorganics; silicone; and mixtures thereof. The particle may include a deposition aid, for example as a coating; the deposition aid may comprise a polymer, for example a cationic polymer.

The fabric treatment compositions of the present disclosure may include a structurant. Structurants may facilitate physical stability of the composition in a container, for example by suspending particles (e.g., of silicone compound droplets, of FCA droplets or encapsulated benefit agents) and/or inhibiting agglomeration/aggregation of such materials. Suitable structurants may include non-polymeric crystalline hydroxyl functional structurants (such as those derived from hydrogenated castor oil), polymeric structuring agents (including those derived from polyacrylates, as well as polymers, which may be relatively linear or cross-linked, derived from cationic monomers selected from the group consisting of methyl chloride quaternized dimethyl aminoethylammonium acrylate, methyl chloride quaternized dimethyl aminoethylammonium methacrylate and mixtures thereof, and non-ionic monomers selected from the group consisting of acrylamide, dimethyl acrylamide and mixtures thereof), cellulosic fibers (for example, microfibrillated cellulose, which may be derived from a bacterial, fungal, or plant origin, including from wood), di-amido gellants, or combinations thereof.

Processes of Making

Consumer product compositions may be made according to conventional processes. For example, a composition, such as a consumer product, may be made by combining a siloxane polymer according to the present disclosure with a consumer product adjunct and/or a carrier. Such processes may be batch processes, continuous-loop processes, and/or in-line mixing processes.

Processes of Treating a Surface

The present disclosure relates to methods of using the above-described polymers and compositions.

Compositions containing the siloxane compounds disclosed herein can be used to clean or treat a surface, such as a fabric. Typically, at least a portion of the surface is contacted with a siloxane polymer or composition of the present disclosure, in neat form or diluted in a liquor, for example, a wash liquor and then the surface may be optionally washed and/or rinsed. In one aspect, a surface is optionally washed and/or rinsed, contacted with a siloxane polymer or composition according to the present disclosure, and then optionally washed and/or rinsed. For purposes of the present invention, washing includes but is not limited to scrubbing and/or mechanical agitation. The fabric may comprise most any fabric capable of being laundered or treated in normal consumer use conditions.

For example, the present disclosure relates to a method of treating a surface, such as a fabric, where the method includes the step of contacting a surface with a siloxane polymer or composition as described herein, preferably a composition, more preferably a fabric treatment composition, even more preferably a liquid fabric conditioning composition. At least a portion of the contacting step may preferably occur in the presence of water, preferably in an automatic washing machine, more preferably during the rinse cycle of an automatic washing machine.

Treatment liquors that may comprise the disclosed compositions may have a pH of from about 3 to about 11.5, or even a pH of from about 5.0 to about 10. The treatment liquor may have a pH that is greater than the pH of the consumer product composition. For example, the consumer product composition may be a liquid composition, preferably a liquid fabric conditioning composition, having a pH of from about 2 to about 4, whereas a treatment liquor, which may be formed by diluting a consumer product composition according to the present disclosure with water, may have a pH of from about 5.0 to about 10. By keeping the pH of the consumer product composition relatively low, it is believed that the siloxane polymer has improved stability.

The disclosed compositions are typically employed at concentrations of from about 500 ppm to about 15,000 ppm in solution. When the wash solvent is water, the water temperature typically ranges from about 5° C. to about 90° C., preferably from about 10° C. to about 50° C., even more preferably from about 15° C. to about 30° C.; relatively lower water temperatures may be preferred for environmental reasons (e.g., to save energy). When the surface includes a fabric, the water to fabric weight ratio is typically from about 1:1 to about 30:1.

Combinations

Specifically contemplated combinations of the disclosure are herein described in the following lettered paragraphs. These combinations are intended to be illustrative in nature and are not intended to be limiting.

A. A consumer product composition comprising a siloxane compound and a consumer product adjunct, wherein the siloxane compound comprises a siloxane backbone and at least one pendant group connected to the siloxane backbone, the at least one pendant group comprising a silyl ether moiety, the silyl ether moiety comprising a perfume raw material fragment, the pendant group further comprising a linker group moiety that links the silyl either moiety to the siloxane backbone, wherein the siloxane compound is further characterized by at least one of the following: a viscosity of from about about 1 cps to about 60,000 cps, or from about 10 cps to about 60,000 cps, or from about 20 cps to about 30,000 cps, or from about 30 cps to about 10,000 cps, or from about 50 cps to about 5,000 cps, or from about 50 cps to about 3000 cps; and/or a number average molecular weight from about 300 to about 100,000 Daltons, or from about 600 to about 100,000 Daltons, or from about 1000 to about 75,000 Daltons, or from about 1200 to about 50,000 Daltons.

B. The consumer product composition according to paragraph A, wherein the silyl ether moiety comprising the perfume raw material fragment is a residue formed upon the reaction of a silanol group with a hydroxyl group of a hydroxyl-group-containing perfume raw material.

C. The consumer product composition according to paragraph A, wherein the silyl ether moiety comprising the perfume raw material fragment is derived from an exchange reaction between a silyl ether group and a hydroxyl group in a perfume raw material.

D. The consumer product composition according to either of paragraphs B or C, wherein the hydroxyl-group-containing perfume raw material comprises an aliphatic alcohol or aromatic alcohol.

E. A consumer product composition comprising a siloxane compound and a consumer product adjunct, wherein the siloxane compound comprises one or more repeat units according to Formula (I):

Formula (I)

wherein:
each $R_1$ is independently selected from the group consisting of H, OH, $C_1$-$C_{32}$ alkyl, $C_1$-$C_{32}$ substituted alkyl, $C_6$-$C_{32}$ aryl, $C_5$-$C_{32}$ substituted aryl, $C_6$-$C_{32}$ alkylaryl, $C_6$-$C_{32}$ substituted alkylaryl, $C_1$-$C_{32}$ alkoxy and $C_1$-$C_{32}$ substituted alkoxy; preferably each $R_1$ is independently selected from the group consisting of H, OH, $C_1$-$C_{16}$ alkyl, $C_1$-$C_4$ alkoxy, more preferably each $R_1$ is independently selected from the group consisting of H, OH, methyl, methoxy, and ethoxy;

each L is a linking bivalent alkylene radical, preferably each L is independently selected from the group consisting of $-(CH_2)_s-$; $-(H_2C)_sOC_6H_4-$;

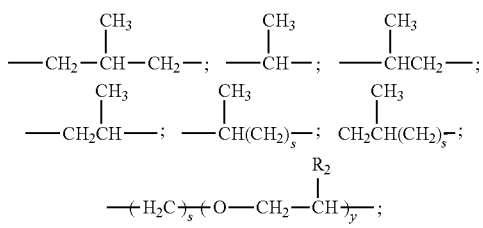

and combinations thereof;

wherein each $R_2$ is independently selected from the group consisting of H, $C_1$-$C_4$ alkyl, substituted alkyl, aryl, substituted aryl, and combinations thereof, preferably H or $C_1$-$C_4$ alkyl, most preferably H or methyl;

each s is independently an integer of from 1 to about 20, preferably each s is independently an integer of from 2 to about 12;

each y is independently an integer of from 1 to about 100, preferably each y is independently an integer of from 1 to about 20, more preferably y is independently an integer of from 1 to about 10;

each Z is independently selected from the group consisting of:

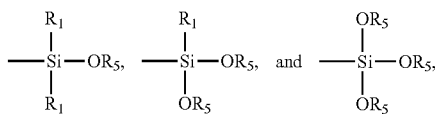

wherein each $R_1$, if present, is independently selected from the group as provided above, and wherein each $R_5$ is independently selected from the group consisting of H, $C_1$-$C_{32}$ alkyl, $C_1$-$C_{32}$ substituted alkyl, $C_6$-$C_{32}$ aryl, $C_5$-$C_{32}$ substituted aryl, $C_6$-$C_{32}$ alkylaryl, and $C_6$-$C_{32}$ substituted alkylaryl, wherein at least one $R_5$ in the siloxane compound is formed from a hydroxyl-group-containing perfume raw material; and wherein index m is an integer of from about 1 to about 500, preferably from about 5 to about 500, or from about 5 to 200, or from about 5 to 100.

F. The consumer product composition according to paragraph E, wherein L is $-(CH_2)_s-$.

G. The consumer product composition according to either of paragraphs E or F, wherein the siloxane compound further comprises one or more repeat units according to Formula (II):

Formula (II)

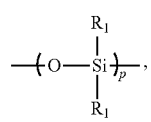

wherein each $R_1$ is independently selected from the group as described above, and wherein index p is an integer of from about 0 to about 500, preferably p is an integer from about 5 to about 400, more preferably p is an integer from about 5 to about 200.

H. The consumer product composition according to paragraph G, wherein the sum of index p+index m is from about 10 to about 1000, or from about 20 to about 1000, preferably from about 20 to about about 200.

I. The consumer product composition according to any of paragraphs G or H, wherein the ratio of p:m is from about 10:1 to about 1:5, preferably from about 5:1 to about 1:4, more preferably from about 3:1 to about 1:3.

J. The consumer product composition according to any of paragraphs E-I, wherein the siloxane compound comprises one or more repeat units according to Formula (III), Formula (IV),

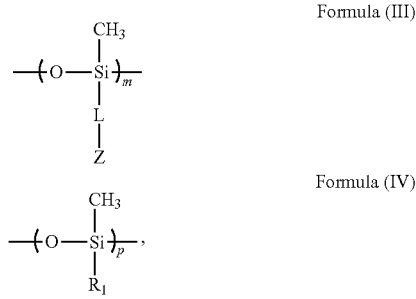

Formula (III)

Formula (IV)

or mixtures thereof.

K. The consumer product composition according to any of paragraphs E-J, wherein $R_1$ is independently selected from $C_1$-$C_{32}$ alkyl groups, preferably independently selected from methyl (C1) groups and $C_2$-$C_{18}$ alkyl groups, more preferably a combination thereof, most preferably wherein the ratio of methyl groups to $C_2$-$C_{18}$ alkyl groups is from about 100:1 to about 10:1.

L. The consumer product composition according to any of paragraphs E-K, wherein the siloxane compound comprises repeat units according to Formula (I), wherein at least one Z moiety, preferably wherein all the Z moieties, is/are selected from the group consisting of:

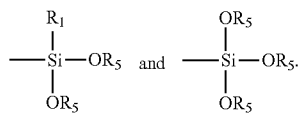

M. the consumer product composition according to any of paragraphs E-L, wherein the siloxane compound comprises repeat units according to Formula (I), wherein at least one Z moiety, or wherein all the Z moieties, is/are

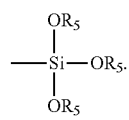

N. The consumer product composition according to any of paragraphs B-M, wherein the hydroxyl group-containing perfume raw material selected from a material in the following table:

| PRM chemical name(s) | Commercial/common name(s) |
|---|---|
| 3,7,11-Trimethyl-2,6,10-dodecatrien-12-ol; 2,6,10-Dodecatrien-1-ol, 3,7,11-trimethyl-; Farnesyl alcohol; 3,7,11-Trimethyl-2,6,10-dodecatrien-1-ol; 3,7,11-Trimethyl-2,6,10-dodecatrienol; Trimethyl-2,6,10-dodecatriene-1-ol; (2E,6E)-3,7,11-Trimethyl-2,6,10-dodecatrien-1-ol; α-Farnesol; alpha-Farnesol; 3,7,11-Trimethyldodeca-2,6,10-trien-1-ol; 3,7,11-Trimethyl-2,6,10-dodecatrien-1-ol (farnesol); (E)-alpha-Farnesol | Farnesol |
| (1-Methyl-2-(1,2,2-trimethylbicyclo[3.1.0]-hex-3-ylmethyl)cyclopropyl)methanol (Mixture of diastereoisomers) | Javanol ® |
| 2-Methyl-3-{(1,7,7-trimethylbicyclo{2.2.1}hept-2-yl)oxy}exo-1-propanol and isomers | Bornafix ® |
| 2-Methyl-4-(2,2,3-trimethylcyclopent-3-en-1-yl)butan-1-ol; 2-Methyl-4-(2,2,3-trimethyl-3-cyclopenten-1-yl)-butan-1-ol | Brahmanol ® |
| 2-Ethyl-4-(2,2,3-trimethyl-3-cyclo-penten-1-yl)-2-buten-1-ol; 2-Ethyl4-(2,2,3-trimethyl-3-cyclopenten-1-yl)-2-buten-1-ol; B-Ethyl-2,2,3-trimethyl-3-Cyclopentene-1-but-2-enol; Ethyl Trimethylcyclopentene Butenol | Bacdanol ® Bacdanol; Sandranol; Bangalol; Sandolen ; Balinol; Laevo Trisandol; Levosandol; |
| Cyclohexanemethanol, 4-(1-methylethyl)-, cis-; 4-Isopropylcyclohexanemethanol; | Mayol ® 957230 |
| 2-Methyl-5-phenylpentan-1-ol | Rosaphen ® |
| 3-Methyl-5-phenylpentanol; 3-Methyl-5-phenyl-1-pentanol; | Phenoxanol ®; Mefrosol; Phenyl hexanol |
| 9-decen-1-ol; 9-Decenol; | Rosalva; Trepanol |
| 2-Methyl-4-(2,2,3-trimethyl-3-cyclopenten-1-yl)-2-buten-1-ol;; 2-Buten-1-ol, 2-methyl-4-(2,2,3-trimethyl-3-cyclopenten-1-yl)-; 2-Buten-1-ol, 2-methyl-4-(2,2,3-trimethyl-3-cyclopenten-1-yl)-3-Cyclohexene-1-propanol gamma 4-dimethyl- | Hindinol; Sandalmysore core; Santalaire; Madranol; Santaliffrm Cyclomethylene citronellol 937001 |
| 2,2-Dimethyl-3-(3-methylphenyl)propan-1-ol | Majantol ® |
| 3,7-Dimethyl-6-octen-1-ol, (-)-Citronellol; Rhodinol | Citronellol |
| (2E,6Z)-nona-2,6-dien-1-ol | 2 6 Nonadienol |
| 2-[(1,7,7-Trimethylbicyclo[2.2.1]hept-2-yl)oxy]-ethanol | Cedanol |
| 2,4,6-Trimethyl-3-cyclohexene-1-methanol | Isocyclogeraniol |
| 3,7-Dimethyl-trans-2,6-octadien-1-ol; 3,7-Dimethyl-2,6-octadien-1-ol (isomers); trans-Geraniol; Guaniol; Lemonol; trans-3,7-Dimethyl-2,6-octadien-1-ol; Geraniol alcohol; Geraniol extra; Geranyl alcohol; 2,6-Dimethyl-trans-2,6-octadien-8-ol; 2,6-Octadien-1-ol, 3,7-dimethyl-, trans-; 3,7-Dimethyl-trans-2,6-octadien-1-ol; (E)-3,7-Dimethyl-2,6-octadien-1-ol; Meranol; trans-3,7-Dimethyl octa-2,6-dien-1-ol; (2E)-3,7-Dimethyl-2,6-octadien-1-ol; Nerol; Neryl alcohol; trans-3,7-Dimethyl-2,6-octadien-1-ol (geraniol); t-Geraniol; (E)-Geraniol; (E)-3,7-Dimethyl-2,6-octadien-1-ol; Geraniol (E) | Geraniol |
| Dihydrocinnamic alcohol; 3-Phenylpropanol; Benzenepropanol; 1-Propanol, 3-phenyl-; γ-Phenylpropanol; γ-Phenylpropyl alcohol; (3-Hydroxypropyl)benzene; Hydrocinnamic alcohol; Hydrocinnamyl alcohol; 3-Phenyl-n-propanol; 3-Phenyl-1-propanol; 3-Phenylpropyl alcohol; 3-Benzenepropanol; Phenylpropyl alcohol; 1-Hydroxy-3-phenylpropane; 3-Phenylpropan-1-ol; Phenylpropylic alcohol | 3-Phenylpropyl alcohol |
| Cinnamic alcohol; 3-Phenyl-2-propen-1-ol; Cinnamyl alcohol; γ-Phenylallyl alcohol; Phenyl-2-propen-1-ol; Styrone; Styryl carbinol; 3-Phenylallyl alcohol; 1-Phenyl-1-propen-3-ol; 3-Phenyl-2-propen-1-ol; 3-Phenyl-2-propenol; Alkohol skoricovy; 3-Fenyl-2-propen-1-ol; Peruvin; Phenyl-2-propenol; Phenylallyl alcohol; (2E)-3-Phenyl-2-propen-1-ol; 3-phenylprop-2-en-1-ol; 2-Propen-1-ol, 3-phenyl- | Cinnamic alcohol |
| 2-Hexen-1-ol, (E)-; trans-2-Hexen-1-ol; trans-2-Hexenol; 2-Hexenol; 2-Hexen-1-ol, trans-; (2E)-2-Hexen-1-ol; (E)-2-Hexenol; (E)-Hex-2-en-1-ol; (E)-Hex-2-enol; (E)-2-Hexene-1-ol; Hex-2(E)-enol; t-2-Hexen-1-ol; 2-(E)-hexenol; trans-Hex-2-en- 1-ol | trans-2-Hexenol |

-continued

| PRM chemical name(s) | Commercial/common name(s) |
|---|---|
| 4-(5,5,6-Trimethylbicyclo[2.2.1]hept-2-yl)cyclohexan-1-ol (and isomers, 85% solution in IPM) | Sandela ® |
| 1-Naphthalenol,1,2,3,4,4a,5,8,8a-octahydro-2,2,6,8-tetramethyl- | Octalynol 967544 |
| 3-Methyl-5-(2,2,3-trimethyl-3-cyclopenten-1-yl)-4-penten-2-ol; | Ebanol |
| 4-Methyl-3-decen-5-ol | Undecavertol |
| 4-Penten-2-ol, 3,3-dimethyl-5-(2,2,3-trimethyl-3-cyclopenten-1-yl)- ; | Nirvanol ® 974650; Polysantol ® 974656 |
| 3-Methyl-4-phenylbutan-2-ol | Muguesia |
| 2-Methoxy-4-allylphenol | Eugenol |
| Cyclohexanepropanol, 2,2,6-trimethyl-alpha-propyl-; 1-(2,2,6-Trimethylcyclohexyl)hexan-3-ol | Norlimbanol 967412; Timberol ®; |
| 5-Propenyl-2-ethoxyphenol; | Propenyl guaethol; Vanitrope |
| 1-(4-Isopropyl-cyclohexyl) ethanol; 1-(4-Isopropylcyclohexyl)-ethanol | Mugetanol |
| 2-Pentylcyclopentan-1-ol; 2-Pentylcyclopentanol | Cyclopentol HC 937165 |
| 3,7,11-Trimethyl-1,6,10-dodecatrien-3-ol | Nerolidol |
| Cedrol Crude | Cedrol |
| 3,7-Dimethyl-7-hydroxyoctan-1-al dimethylacetal | Hydroxycitronellal dimethylacetal |
| 4-Methyl-2-(2-methylpropyl)tetrahydro-2H-pyran-4-ol; Florol ® 966458 | Florosa |
| 2,5,5-Trimethyl-octahydronaphthalen-2-ol; 2,5,5-Trimethyl-1,2,3,4,4α,5,6,7-octahydro-2-naphthalenol | Ambrinol 20-T Ambrinol; Ambrino S |
| 4-Methyl-1-isopropyl-3-cyclohexen-1-ol | Terpinen-4-ol |
| 3,7-Dimethyl-1,6-nonadien-3-ol (cis & trans) | Ethyl linalool |
| 1-Methyl-3-(2-methylpropyl)cyclohexanol | Rossitol ® |
| 4-Phenyl-2-methyl-2-butanol | α,α-Dimethylphenyl-ethylcarbinol |
| 3,7-Dimethyloctan-1,7-diol | Hydroxyol |
| 1-Methyl-4-isopropylcyclohexane-8-ol | Dihydro terpineol |
| 3,7-Dimethyl-1,6-octadiene-3-ol | Linalool |
| 3,7-Dimethyl-4,6-octadien-3-ol | Allo-Ocimenol; Muguol |
| 2-(4-Methyl-cyclohex-3-enyl)-propan-2-ol; p-Menthan-8-ol | alpha Terpineol, Lindenol ™ |
| 1-Phenyl-2-methyl-2-propanol; α,α-Dimethylbenzyl carbinol; benzeneethanol, α,α-dimethyl- | 2-methyl-1-phenylpropan-2-ol |
| Cyclohexanepropanol,2,2-dimethyl- | Coranol 928130 |
| 2,6-Dimethyl-7-octen-2-ol; 2-Methyl-6-methyleneoct-7-en-2-ol, dihydro derivative; 7-Octen-2-ol, 2,6-dimethyl-; 2,6-Dimethyl-7-octen-2-ol; 3,7-Dimethyl-1-octen-7-ol; 2,6-Dimethyl-oct-7-en-2-ol; Mircenol, 6,10-dihydro | Dihydromyrcenol, Dihydro Myrcenol |
| 3,7-Dimethyloctan-3-ol | Tetrahydrolinalool |
| 2,6-Dimethyl-2-octanol | Tetrahydro myrcenol |
| 2,6-Dimethyl-2-heptanol | Dimetol, Freesiol, Lolitol |
| 2-Hexen-1-ol | Beta Gamma Hexenol |
| 3-Hexen-1-ol | Beta Gamma Hexenol |
| Ethanol, 2,2'-oxybis- | Calone 161 |
| Benzoic acid, 2-amino-, methyl ester | Methyl Anthranilate |
| 4,7-Methano-1H-inden-6-ol, 3a,4,5,6,7,7a-hexahydro-, acetate | Flor Acetate |
| 2(3H)-Furanone, 5-ethyldihydro- | Gamma Hexalactone |
| Phenol, 4-methyl- | Para Cresol |
| 2H-Pyran, 3,6-dihydro-4-methyl-2-(2-methyl-1-propenyl)- | Nerol Oxide |
| Benzeneethanol, .beta.-methyl- | Hydratropic Alcohol |
| Benzeneethanol, .alpha., .alpha.-dimethyl- | Dimethyl Benzyl Carbinol |
| Benzoic acid, 2-(methylamino)-, methyl ester | Dimethyl Anthranilate |
| 4H-Pyran-4-one, 2-ethyl-3-hydroxy- | Ethyl Maltol |
| 1-Heptanol | Heptyl Alcohol |
| Ethanol, 2-(2-methoxyethoxy)- | Veramoss Sps |
| Cyclohexaneethanol | Cyclohexyl Ethyl Alcohol |
| 4-Hydroxy-3-methoxybenzaldehyde | Vanillin |
| 3-Ethoxy-4-hydroxybenzaldehyde | Ethyl Vanillin | preferably wherein the hydroxyl-containing perfume raw material is selected from geraniol, 2,6-nonadienol, cinnamic alcohol, linalool, flor acetate, dihydromyrcenol, derivatives thereof, or mixtures thereof.

O. The consumer product composition according to any of paragraphs A-N, wherein the siloxane compound is formed from a parent silicone compound, wherein the viscosity of the parent silicone compound before attachment of the perfume raw material fragment is from about 10 cps to about 60,000 cps, or from about 20 cps to about 30,000 cps, or from about 30 cps to about 10,000 cps, or from about 50 cps to about 5,000 cps, or from about 50 cps to about 3000 cps.

P. A consumer product composition according to any of paragraphs A-O, wherein the composition comprises from about from about 0.1% to about 20%, by weight of the composition of the siloxane compound, preferably from about 0.1% to about 10%, more preferably from about 0.1% to about 5%, or from about 0.1% to about 3%, or from about 0.1% to about 1%.

Q. A consumer product composition according to any of paragraphs A-P, wherein the consumer product composition is characterized by a pH of from about 2 to about 12, or from about 2 to about 8.5, or from about 2 to about 7, or from about 2 to about 5, or from about 2 to about 4, preferably a pH of from about 2 to about 3.7, more preferably a pH from about 2 to about 3.5,
  wherein the pH is determined by dissolving/dispersing the composition in deionized water to form a solution at 10% concentration, at about 20° C.

R. The consumer product composition according to any of paragraphs A-Q, wherein the consumer product composition comprises may comprise at least about 50%, preferably at least about 75%, more preferably at least about 85%, by weight of the composition, of water.

S. The consumer product composition according to any of paragraphs A-R, wherein the consumer product adjunct is selected from the group consisting of bleach activators, surfactants, delivery enhancing agents, builders, chelating agents, dye transfer inhibiting agents, dispersants, enzymes, enzyme stabilizers, catalytic metal complexes, polymeric dispersing agents, clay and soil removal/anti-redeposition agents, brighteners, suds suppressors, dyes, additional perfumes and/or perfume delivery systems, structure elasticizing agents, fabric conditioning actives (FCAs), anionic surfactant scavengers, carriers, hydrotropes, processing aids, structurants, anti-agglomeration agents, coatings, formaldehyde scavengers, deposition aids, emulsifiers, pigments, or mixtures thereof.

T. A consumer product composition according to any of paragraphs A-S, wherein the consumer product adjunct comprises a fabric conditioning active (FCA), preferably an FCA selected from quaternary ammonium ester compounds, silicones, non-ester quaternary ammonium compounds, amines, fatty esters, sucrose esters, silicones, dispersible polyolefins, polysaccharides, fatty acids, softening or conditioning oils, polymer latexes, or combinations thereof, more preferably quaternary ammonium ester compounds.

U. The consumer product composition according to any of paragraphs A-T, wherein the consumer product composition is in the form of a liquid composition, a granular composition, a single-compartment pouch, a multi-compartment pouch, a dissolvable sheet, a pastille or bead, a fibrous article, a tablet, a bar, a flake, a foam/mousse, a non-woven sheet, or a mixture thereof, preferably a liquid, solid, or combination thereof, more preferably a liquid.

V. The consumer product composition according to any of paragraphs A-U, wherein the consumer product composition is a beauty care composition, a fabric care composition, a home care composition, or a combination thereof, preferably a fabric care composition, more preferably wherein the fabric care composition is selected from a laundry detergent composition, a fabric conditioning composition, a laundry and rinse additive, a fabric pre-treatment composition, a fabric refresher composition, or a combination thereof, even more preferably wherein the fabric care composition is a fabric conditioning composition, most preferably a liquid fabric conditioning composition.

W. A siloxane compound as described in any of paragraphs A-O.

X. A method of treating a surface with the consumer product composition according to any of paragraphs A-V, comprising the step of contacting the surface, preferably a fabric, with the consumer product composition, optionally in the presence of water.

Test Methods

Viscosity Test Method

A preliminary estimate of the sample viscosity at 25° C. is used to select the appropriate instrument geometry to be used during the final viscosity measurement analyses, which are conducted on a model AR-G2 Rheometer (manufactured by TA Instruments Corp., New Castle, Del., USA). A preliminary estimate of the sample viscosity may be obtained by using a Brookfield Viscometer (Brookfield Engineering Laboratories Inc., Middleboro, Mass., USA). The selection of geometry for use on the AR-G2 Rheometer is determined in accordance with the following table:

| AR-G2 Geometry Selection | |
|---|---|
| Preliminary Estimate of Sample Viscosity | AR-G2 Geometry and Plate Size |
| >1000 Pa*s | 25 mm parallel plate |
| 1 to 1000 Pa*s | 40 mm parallel plate |
| >Water-thin to < 1 Pa*s | 60 mm parallel plate |
| Water-thin | Couette/Cup and Bob |

The geometry attached to the instrument, the instrument is mapped, the gap distance is zeroed, and the instrument temperature is set to 25° C. The measurement mode is selected as Stiff Mode when using parallel plates, or to Soft mode when using the couett cup and bob geometry. Sample material is mounted into the sample holding geometry e.g., the base plate. The minimum gap distance allowable between the base plate and the selected geometry is 10× the diameter of the largest common particle present in sample. If there are common particles in the sample which have a diameter greater than 100 μm (as determined microscopically), then the gap value is set to 10× the diameter of the largest common particle, otherwise the gap distance is set to the default value of 1000 μm (ie 1 mm). The selected geometry is lowered to the appropriate gap and a plastic tool is used to trim off any excess sample material. The sample material is allowed to equilibrate to the temperature of the instrument. Three rheological measurement analyses are conducted, namely: Flow Curve, Stress Sweep, and Frequency Sweep, using the following selections and settings:
  Flow Curve: select Stepped Flow 0.01 to 100; 10 pts/decade; shear stress; constant time 20; average last 10.
  Stress Sweep: set the Stress Range as 0.01 to 100 Pa; set the Frequency at 1 rad/s.

Frequency Sweep: Set the Angular Frequency Range as 0.1 to 100.

To ensure that the analysis is conducted within the Linear Viscoelastic Region set the Stress value at a third of the stress value that was present when G' started to degrade during the prior Stress Sweep analysis.

Silicone Molecular Weight

Quantitative $^{29}$Si NMR data can be acquired using an NMR spectrometer equipped with a 5 mm PABBO Z-GRD probe, such as instrument model Avance III HD 400 MHz (Bruker Corp., Billerica, Mass., USA), or equivalent. The ratio of terminal silicon atoms (trimethylsiloxane) to non-terminal silicon atoms (dimethylsiloxane) can be used to determined number molecular weight.

Siloxane Compound Emulsification

An emulsion of the siloxane compounds of the present disclosure may be prepared according to the following procedure.

Provide 60.0 parts of the siloxane compound. Add Softanol 70™ (2.5 parts; ex Nippon Shokubai Co., LTD.) and Tomadol™ 25-7 (4.0 parts; ex Evonik Industries) to the siloxane compound. The mixture is mixed for 1 minute with a FlackTec Inc. SpeedMixer DAC 150 FVZ-K at 3500 rpm. Water (33.5 parts total) is added in three equal, separate additions, and the mixture mixed with the SpeedMixer after each water addition.

Fabric Softener Preparation

To an 9.5 wt % N,N di(tallowoyloxyethyl)-N,N dimethylammonium chloride in water mixture, the siloxane compound emulsion is added in an amount such that the concentration of the perfume raw material or perfume raw material fragment in the fabric softener is about 0.3 wt % after the fabric softener preparation. The mixture is stirred for 5 min with an IKA RW 20 D S1 Mixer, Model RW20D-S1, and IKA R1342 impeller blade at 350 rpm. A structurant and a deposition aid is added, and the mixture is stirred for 10 min. Water is added if needed to standardize the concentration of N,N di(tallowoyloxyethyl)-N,N dimethylammonium chloride amongst test legs to 8 wt %, and the mixture stirred for 5 min. The pH is adjusted to 2-3 with 1N HCl.

Fabric Preparation

To prepare fabrics for Headspace analysis testing, fabric samples (100% Cotton Terry Cloth, Item Number ITL 1022-15PGP, Calderon Textiles, Inc. 6131 W. 80$^{th}$ St., Indianapolis, Ind. 46278, Desized and conditioned with 3 wash cycles of Detergent and Fabric Softener) are treated with the Fabric Softener formulas in a manner consistent with North American consumers via clothes mini-washing machines and clothes dryers. Fabric is equilibrated at 21.1° C. and 50% Relative Humidity for 24 hours prior to Headspace analysis. Treatment conditions are as follows:

Wash: 12 min agitation, 30.6° C.
Rinse: 2 min agitation, 15.6° C.
Water Hardness: 103 mg/L
Water: 7.6 L
Fabric Load Weight: 290 g
Tumble Dry Setting: High, Cotton
Detergent Dose: 9.96 g
Fabric Softener Dose: 5.68 g Headspace Analysis Above Fabrics To determine the level of perfume raw material in the headspace above a fabric, the following procedure is used.

The following equipment is used: Gas Chromatograph 7890B equipped with a Mass Selective Detector (5977B) (MSD) and Chemstation quantitation package; Gerstel Multi-Purpose sampler equipped with a solid phase micro-extraction (SPME) probe or similar system; Divinylbenzene/Carboxen/Polydimethylsiloxane SPME fiber from Supleco part #57298-U (or similar fiber); 30 m×0.25 mm nominal diameter, 0.25 m film thickness, J&W 122-5532UI DB-5; 20 mL headspace vials.

To prepare the fabric for analysis, Cut three 2.54 cm×5.08 cm cotton swatches from the cotton terry that is prepared and treated according to the above methods. Place each piece in a 20 mL headspace vial and cap.

The Gerstel auto sampler parameters are as follows: SPME—from Incubator; Incubation Temperature—65° C.; Incubation Time—10.00 min SAMPLE PARAMETERS; Vial Penetration—22.00 mm; Extraction Time—5.00 min; Inj. Penetration—54.00 mm; Desorption Time—300 s.

The GC oven parameters are as follows for the Front SS Inlet He: Mode—Splitless; Heater—270° C.; GC Run Time—14.28 min. For the Oven: Initial temp.—40° C.; Hold Time—0.5 min; Heating Program—Rate of 17° C./min, Temp of 270° C., Hold Time of 0.25 min.

The MSD parameters are as follows: Run in scan mode with a minimum range of 35 to 350 m/z; Calibration curves are generated from the standards perfume material. Chemstation software (or similar quantitation software) calculates the mass amount in the headspace using the calibration curve for each perfume component.

Headspace Analysis Above Fabric Softener

To determine the level of perfume raw material in the headspace above a fabric softener composition, the same general procedure is followed as for Headspace Analysis Above a Fabric (see above), with the following changes.

Prepare the composition samples for analysis (three replicates) by placing about one gram of neat product into a 20 mL headspace vial and cap.

For the Gerstel auto sampler parameters: Incubation Temperature—30° C.; Vial Penetration—25.00 mm. For the GC Oven parameters, for the Front SS Inlet He: Mode—Split—250:1.

For the MSD parameters: Run in scan mode with a minimum range of 35 to 350 m/z; use Chemstation software (or similar software) measure the target ion area response for each perfume component.

EXAMPLES

The examples provided below are intended to be illustrative in nature and are not intended to be limiting.

Synthesis Examples

Synthesis Examples 1 through 7 are illustrative examples of making siloxane compounds according to the present disclosure. FIG. 1 is a table showing the structures of the synthesized siloxane compounds according to the Synthesis Examples below.

Synthesis Example 1

Vinyltrimethoxysilane (81.00 g; Item #235768; available from Sigma-Aldrich, St. Louis, Mo.), geraniol (251.75 g; Geraniol 980 Pure; available from International Flavors and Fragrances, 521 West 57th Street New York, N.Y.) and sodium methoxide, 25 wt. % in methanol (0.38 g; Item #156256; available from Sigma-Aldrich, St. Louis, Mo.) are combined in a three-necked round-bottomed reaction flask with stirring and light nitrogen sweep. Temperature is slowly increased to 70° C. at a rate and at a nitrogen sweep velocity such that methanol is removed from the flask and geraniol is not. Once at 70° C., the nitrogen sweep, mixing and 70° C. reaction temperature is maintained for 18 hours. The mixture is cooled, acetic acid (0.12 g) added while mixing and any precipitate removed via centrifugation to yield the vinyl trigeraniol alkoxy intermediate.

The vinyl trigeraniol alkoxy intermediate (50.00 g) and methylhydrosiloxane-dimethylsiloxane copolymer, trimethylsiloxy terminated (9.83 g; HMS-301; available from Gelest, Morrisville, Pa.) are combined in a three-necked round-bottomed reaction flask with stirring, heated to 80° C. and 1 wt % chloroplatinic acid in 2-propanol (0.62 g; chloroplatinic acid Item #520896; available from Sigma-Aldrich, St. Louis, Mo.) is added dropwise. The mixture is heated at 90° C. for 2 hours. An additional 0.27 g of 1 wt % chloroplatinic acid in 2-propanol is added and the mixture is heated for 6 hours, with stirring, at 90° C. to yield the siloxane compound. $^1$H NMR analysis indicated a geraniol fragment activity of 61 wt %.

Synthesis Example 2

Triethylamine (33.48 g; Item # T0886; available from Sigma-Aldrich, St. Louis, Mo.), geraniol (50.01 g; Geraniol 980 Pure; available from International Flavors and Fragrances, 521 West 57th Street New York, N.Y.) and toluene (200 mL g; Item #179418; available from Sigma-Aldrich, St. Louis, Mo.) are combined in a three-necked round-bottomed reaction flask with stirring. Dichloromethylvinylsilane, (22.93 g; Item #104914; available from Sigma-Aldrich, St. Louis, Mo.) is added dropwise at a rate such that a temperature of the solution between 40-50° C. is maintained. The mixture is cooled to ambient, stirred for 1 hour, filtered through Whatman qualitative filter paper, Grade 4 and stripped of toluene and triethylamine under reduced pressure via rotary evaporation at 70° C. to yield the vinyl digeraniol alkoxy intermediate.

The vinyl digeraniol alkoxy intermediate (20.48 g) and methylhydrosiloxane-dimethylsiloxane copolymer, trimethylsiloxy terminated (13.27 g; HMS-301; available from Gelest, Morrisville, Pa.) are combined in a three-necked round-bottomed reaction flask with stirring, heated to 80° C. and 1 wt % chloroplatinic acid in 2-propanol (0.43 g; chloroplatinic acid Item #520896; available from Sigma-Aldrich, St. Louis, Mo.) is added dropwise. The mixture is heated at 90° C. for 4 hours. An additional 0.15 g of 1 wt % chloroplatinic acid in 2-propanol is added and the mixture is heated for 6 hours, with stirring, at 90° C. to yield the siloxane compound. $^1$H NMR analysis indicated a geraniol fragment activity of 50 wt %.

Synthesis Example 3

Triethylamine (12.87 g; Item # T0886; available from Sigma-Aldrich, St. Louis, Mo.), geraniol (19.22 g; Geraniol 980 Pure; available from International Flavors and Fragrances, 521 West 57th Street New York, N.Y.) and toluene (90 g; Item #179418; available from Sigma-Aldrich, St. Louis, Mo.) are combined in a three-necked round-bottomed reaction flask with stirring. Chlorodimethylvinylsilane, (14.98 g; Item #395439; available from Sigma-Aldrich, St. Louis, Mo.) is added dropwise at a rate such that a temperature of the solution between 40-50° C. is maintained. The mixture is cooled to ambient, stirred for 1 hour, filtered through Whatman qualitative filter paper, Grade 4 and stripped of toluene and triethylamine under reduced pressure via rotary evaporation at 70° C. to yield the vinyl monogeraniol alkoxy intermediate.

The vinyl monogeraniol alkoxy intermediate (10.06 g) and methylhydrosiloxane-dimethylsiloxane copolymer, trimethylsiloxy terminated (9.83 g; HMS-301; available from Gelest, Morrisville, Pa.) are combined in a three-necked round-bottomed reaction flask with stirring and chloroplatinic acid, 1 wt % in 2-propanol (0.70 g; chloroplatinic acid Item #520896; available from Sigma-Aldrich, St. Louis, Mo.) is added and the mixture is heated to 97° C. for 1 hour. An additional 0.20 g of 1 wt % chloroplatinic acid in 2-propanol is added and the mixture is heated overnight, with stirring, at 80° C. to yield the siloxane compound. $^1$H NMR analysis indicated a geraniol fragment activity of 32 wt %.

Synthesis Example 4

Triethylamine (67.2 g; Item # T0886; available from Sigma-Aldrich, St. Louis, Mo.), geraniol (100.11 g; Geraniol 980 Pure; available from International Flavors and Fragrances, 521 West 57th Street New York, N.Y.) and toluene (600 mL g; Item #179418; available from Sigma-Aldrich, St. Louis, Mo.) are combined in a three-necked round-bottomed reaction flask with stirring. Dichloromethylvinylsilane, (22.93 g; Item #104914; available from Sigma-Aldrich, St. Louis, Mo.) is added dropwise at a rate such that a temperature of the solution between 50-60° C. is maintained. The mixture is cooled to ambient, stirred for 1 hour, filtered through Whatman qualitative filter paper, Grade 4 and stripped of toluene and triethylamine under reduced pressure via rotary evaporation at 70° C. to yield the vinyl digeraniol alkoxy intermediate.

The vinyl digeraniol alkoxy intermediate (25.01 g) and methylhydrosiloxane-dimethylsiloxane copolymer, trimethylsiloxy terminated (28.22 g; HMS-151; available from Gelest, Morrisville, Pa.) are combined in a three-necked round-bottomed reaction flask with stirring, heated to 50° C. and 1 wt % chloroplatinic acid in 2-propanol (0.38 g; chloroplatinic acid Item #520896; available from Sigma-Aldrich, St. Louis, Mo.) is added dropwise. The mixture is heated at 80° C. for 15 minutes. An additional 0.21 g of 1 wt % chloroplatinic acid in 2-propanol is added and the mixture is heated for 16 hours, with stirring, at 80° C. to yield the siloxane compound. $^1$H NMR analysis indicated a geraniol fragment activity of 35 wt %.

Synthesis Example 5

Allyltrimethoxysilane (35.06 g; Item #679267; available from Sigma-Aldrich, St. Louis, Mo.), geraniol (100.00 g; Geraniol 980 Pure; available from International Flavors and Fragrances, 521 West 57th Street New York, N.Y.) and sodium methoxide, 25 wt. % in methanol (0.34 g; Item #156256; available from Sigma-Aldrich, St. Louis, Mo.) are combined in a three-necked round-bottomed reaction flask with stirring and light nitrogen sweep. Temperature is slowly increased to 70° C. at a rate and nitrogen sweep velocity such that methanol is removed from the flask and geraniol is not. Once at 70° C., the nitrogen sweep, mixing and 70° C. reaction temperature is maintained for 18 hours. The mixture is cooled, acetic acid (0.11 g) added while mixing and any precipitate removed via centrifugation to yield the allyl trigeraniol alkoxy intermediate.

The allyl trigeraniol alkoxy intermediate (50.00 g) and methylhydrosiloxane-dimethylsiloxane copolymer, trimethylsiloxy terminated (23.16 g; HMS-301; available from Gelest, Morrisville, Pa.) are combined in a three-necked round-bottomed reaction flask with stirring, heated to 80° C.

and 1 wt % chloroplatinic acid in 2-propanol (0.50 g; chloroplatinic acid Item #520896; available from Sigma-Aldrich, St. Louis, Mo.) is added dropwise. The mixture is heated at 90° C. for 2 hours. An additional 0.20 g of 1 wt % chloroplatinic acid in 2-propanol is added and the mixture is heated for 6 hours, with stirring, at 90° C. to yield the siloxane compound. Geraniol fragment activity is 60 wt %.

Synthesis Example 6

Vinyltrimethoxysilane (15.24 g; Item #235768; available from Sigma-Aldrich, St. Louis, Mo.), (E,Z)-2,6-nonadien-1-ol (44.88 g; available from Bedoukian, Danbury, Conn.) and sodium methoxide, 25 wt. % in methanol (0.08 g; Item #156256; available from Sigma-Aldrich, St. Louis, Mo.) are combined in a three-necked round-bottomed reaction flask with stirring and light nitrogen sweep. Temperature is slowly increased to 115° C. at a rate and nitrogen sweep velocity such that methanol is removed from the flask and (E,Z)-2,6-nonadien-1-ol is not. Once at 115° C., the nitrogen sweep, mixing and 115° C. reaction temperature is maintained for 16 hours. The mixture is cooled, acetic acid (0.03 g) added while mixing and any precipitate removed via centrifugation to yield the vinyl trinonadienol alkoxy intermediate.

The vinyl trinonadienol alkoxy intermediate (49.95 g) and methylhydrosiloxane-dimethylsiloxane copolymer, trimethylsiloxy terminated (25.50 g; HMS-301; available from Gelest, Morrisville, Pa.) are combined in a three-necked round-bottomed reaction flask with stirring, heated to 80° C. and 1 wt % chloroplatinic acid in 2-propanol (1.26 g; chloroplatinic acid Item #520896; available from Sigma-Aldrich, St. Louis, Mo.) is added dropwise. The mixture is heated at 90° C. for 16 hours. $^1$H NMR analysis indicated a geraniol fragment activity of 58 wt %.

Synthesis Example 7

Vinyltrimethoxysilane (81.00 g; Item #235768; available from Sigma-Aldrich, St. Louis, Mo.), geraniol (251.75 g; Geraniol 980 Pure; available from International Flavors and Fragrances, 521 West 57th Street New York, N.Y.) and sodium methoxide, 25 wt. % in methanol (0.38 g; Item #156256; available from Sigma-Aldrich, St. Louis, Mo.) are combined in a three-necked round-bottomed reaction flask with stirring and light nitrogen sweep. Temperature is slowly increased to 70° C. at a rate and nitrogen sweep velocity such that methanol is removed from the flask and geraniol is not. Once at 70° C., the nitrogen sweep, mixing and 70° C. reaction temperature is maintained for 18 hours. The mixture is cooled, acetic acid (0.12 g) added while mixing and any precipitate removed via centrifugation to yield the vinyl trigeraniol alkoxy intermediate.

The vinyl trigeraniol alkoxy intermediate (50.00 g) and methylhydrosiloxane-dimethylsiloxane copolymer, trimethylsiloxy terminated (9.83 g; HMS-301; available from Gelest, Morrisville, Pa.) are combined in a three-necked round-bottomed reaction flask with stirring, heated to 80° C. and 1 wt % chloroplatinic acid in 2-propanol (0.62 g; chloroplatinic acid Item #520896; available from Sigma-Aldrich, St. Louis, Mo.) is added dropwise. The mixture is heated at 90° C. for 2 hours. 1-Octene (0.45 g; Item #04806; available from Sigma-Aldrich, St. Louis, Mo.) is added, an additional 0.27 g of 1 wt % chloroplatinic acid in 2-propanol is added and the mixture heated for 6 hours, with stirring, at 90° C. Excess 1-octene is removed under elevated temperature and reduced pressure to yield the siloxane compound. Geraniol fragment activity is about 60 wt %.

Performance Examples

Performance Examples 1-3 are illustrative examples that show the performance and/or stability benefits of the siloxane compounds, consumer products, and/or processes described herein.

Performance Example 1. Droplet Size

The droplet size for the siloxane compounds from Synthesis Examples 1-4 and 6 are analyzed as the emulsion and in the fabric softener utilizing a Horiba, partica, Laser Scattering, Particle Size Distribution Analyzer LA-950V2 with a static quartz cell and operated in accordance with the manufacturer's instructions.

| Siloxane Compound | Droplet size as Emulsion | Droplet Size in fabric softener |
| --- | --- | --- |
| Synthesis Example 1 | 0.70 | 0.56 |
| Synthesis Example 2 | 0.65 | 0.52 |
| Synthesis Example 3 | 1.16 | 0.83 |
| Synthesis Example 4 | 0.62 | 0.51 |
| Synthesis Example 6 | 1.29 | 0.80 |

The results in the above table show the relative ease of emulsification and formulatability of the siloxane compounds in a fabric softener composition.

Performance Example 2. Headspace Above Fabric Softener Composition

The concentration of perfume raw material is determined in the headspace above the fabric softener after storage at 35° C., according to the included procedure.

| Additive | Relative Concentration of Perfume raw material in the Headspace Above the Fabric Softener (area response) after preparation 27 hours at ambient after preparation |
| --- | --- |
| Synthesis Example 1 | 2598 |
| Synthesis Example 2 | 1435 |
| Synthesis Example 3 | 17237 |
| Synthesis Example 4 | 9207 |
| Synthesis Example 6 | 1779 |
| Geraniol—Free form | 132788 |
| (E,Z)-2,6-nonadien-1-ol-Free form | 133864 |
| No perfume raw material or perfume raw material fragment | 286 |

The results in the above table show lower perfume concentration in the headspace for siloxane compounds of the present invention, showing superior chemical stability to hydrolysis.

Performance Example 3. Headspace Above Fabrics

Siloxane compounds from Synthesis Examples 1-4 and 6 are emulsified and formulated into fabric softener, such that the concentration of the perfume raw material or perfume raw material fragment in the fabric softener is 0.3 wt %, according to the included procedures. Fabrics are treated with the fabric softeners containing the siloxane compounds, equilibrated for 16 hours at 21.1° C. and 50% relative humidity and concentration of perfume raw material determined in the headspace above the fabric, all according to the included procedures.

Fabric softeners are also separately prepared containing geraniol and (E,Z)-2,6-nonadien-1-ol in free form, at 0.3 wt %, and without any perfume raw material or perfume raw material fragment, all according to the included procedures.

| Additive | Concentration of Perfume raw material in the Headspace Above the Fabric (nmol/L) |
|---|---|
| Synthesis Example 1 | 39.83 |
| Synthesis Example 2 | 17.84 |
| Synthesis Example 3 | 6.94 |
| Synthesis Example 4 | 17.85 |
| Synthesis Example 6 | 10.02 |
| Geraniol—Free form | 1.46 |
| (E,Z)-2,6-nonadien-1-ol—Free form | None Detected |
| No perfume raw material or perfume raw material fragment | None Detected |

The results in the above table show that these improved siloxane compounds give significantly higher concentration of perfume alcohol in the headspace above fabric.

Composition Examples

The following formulations are illustrative consumer product compositions that include siloxane polymers according to the present disclosure. The consumer products may be made according to conventional methods, and may be used in the manner that such types of consumer products are typically used. All ingredient levels are provided as weight percent, by weight of the composition, unless otherwise indicated.

Composition Example 1. Liquid Fabric Conditioning Compositions

Liquid fabric conditioning compositions are prepared by mixing together ingredients shown below in the following table.

| Ingredients | 1A | 1B |
|---|---|---|
| Fabric Softener Active[1] | 8.0 | 7.5 |
| Quaternized polyacrylamide | 0.135 | 0.135 |
| Siloxane polymer from any of Synthesis Examples 1-7 | 4.0 | 3.0 |
| Water soluble dialkyl quat | 0.7 | 0.2 |
| Water and minors (e.g., emulsifiers, perfume, suds suppressor, stabilizers, preservative, antioxidant, chelant, pH control agents, buffers, dyes &/or other optional ingredients) | q.s. to 100% pH = 3.0 | q.s. to 100% pH = 3.0 |

[1]Any of the following FSAs: N,N-di(tallowoyloxyethyl)-N,N-dimethylammonium chloride; methyl bis(tallow amidoethyl)2-hydroxyethyl ammonium methyl sulfate; and/or compound of Fatty acid with Methyldiethanolamine in a molar ratio 1.5:1, quaternized with Methylchloride, resulting in a 1:1 molar mixture of N,N-bis(stearoyl-oxy-ethyl) N,N-dimethyl ammonium chloride and N-(stearoyl-oxy-ethyl) N,-hydroxyethyl N,N dimethyl ammonium chloride.

Composition Example 2. Liquid Fabric Enhancers

Liquid Fabric Enhancers are prepared by mixing together ingredients shown below in the following table.

| Ingredient | 2A | 2B | 2C | 2D | 2E | 2F | 2G | 2H | 2I | 2J |
|---|---|---|---|---|---|---|---|---|---|---|
| FSA[a] | 14 | 16.47 | 14 | 12 | 12 | 16.5 | — | — | 5 | 5 |
| FSA[b] | | | | | — | | 3.00 | — | — | — |
| FSA[c] | | | | | — | | — | 6.5 | — | — |
| Ethanol | 2.18 | 2.57 | 2.18 | 1.95 | 1.95 | 2.57 | — | — | 0.81 | 0.81 |
| Isopropyl Alcohol | — | — | — | — | — | — | 0.33 | 1.22 | — | — |
| Starch[d] | 1.25 | 1.47 | 2.00 | 1.25 | — | 2.30 | 0.5 | 0.70 | 0.71 | 0.42 |
| Silicone compound according to Synthesis Examples 1-7 | 0.6 | 0.75 | 0.6 | 2.0 | 0.37 | 3.0 | 0.37 | 0.6 | 1.0 | 0.37 |
| Phase Stabilizing Polymer[f] | 0.21 | 0.25 | 0.21 | 0.21 | 0.14 | — | — | 0.14 | — | — |
| Calcium Chloride | 0.15 | 0.176 | 0.15 | 0.15 | 0.30 | 0.176 | — | 0.1-0.15 | — | — |
| DTPA[h] | 0.017 | 0.017 | 0.017 | 0.017 | 0.007 | 0.007 | 0.20 | — | 0.002 | 0.002 |
| Preservative (ppm)[i,j] | 5 | 5 | 5 | 5 | 5 | 5 | — | 250[j] | 5 | 5 |
| Antifoam[k] | 0.015 | 0.018 | 0.015 | 0.015 | 0.015 | 0.015 | — | 0.1 | 0.015 | 0.015 |
| Dye (ppm) | 40 | 40 | 40 | 40 | 40 | 40 | 11 | 30-300 | 30 | 30 |
| Ammonium Chloride | 0.100 | 0.118 | 0.100 | 0.100 | 0.115 | 0.115 | — | — | — | — |

-continued

| Ingredient | 2A | 2B | 2C | 2D | 2E | 2F | 2G | 2H | 21 | 2J |
|---|---|---|---|---|---|---|---|---|---|---|
| HCl | 0.012 | 0.014 | 0.012 | 0.012 | 0.028 | 0.028 | 0.016 | 0.025 | 0.011 | 0.011 |
| Structurant [l] | 0.01 | 0.01 | 0.01 | 0.01 | 0.01 | 0.01 | 0.01 | 0.01 | 0.01 | 0.01 |
| Perfume | 0.8 | 0.7 | 0.9 | 0.5 | 1.2 | 0.5 | 1.1 | 0.6 | 1.0 | 0.9 |
| Deionized Water | | | | | To balance (pH is about 3) | | | | | |

[a] N,N-di(tallowoyloxyethyl)-N,N-dimethylammonium chloride.
[b] Methyl bis(tallow amidoethyl)2-hydroxyethyl ammonium methyl sulfate.
[c] Compound of Fatty acid with Methyldiethanolamine in a molar ratio 1.5:1, quaternized with Methylchloride, resulting in a 1:1 molar mixture of N,N-bis(stearoyl-oxy-ethyl) N,N-dimethyl ammonium chloride and N-(stearoyl-oxy-ethyl) N,-hydroxyethyl N,N dimethyl ammonium chloride.
[d] Cationic high amylose maize starch available from National Starch under the trade name CATO ®.
[f] Copolymer of ethylene oxide and terephthalate having the formula described in U.S. Pat. No. 5,574,179 at col. 15, lines 1-5, wherein each X is methyl, each n is 40, u is 4, each R1 is essentially 1,4-phenylene moieties, each R2 is essentially ethylene, 1,2-propylene moieties, or mixtures thereof.
[g] SE39 from Wacker
[h] Diethylenetriaminepentaacetic acid.
[i] KATHON ® CG available from Rohm and Haas Co. "PPM" is "parts per million."
[j] Gluteraldehyde
[k] Silicone antifoam agent available from Dow Corning Corp. under the trade name DC2310.
[l] Hydrophobically-modified ethoxylated urethane available from Rohm and Haas under the tradename Aculan 44.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A consumer product composition comprising a siloxane compound and a consumer product adjunct,
   wherein the siloxane compound comprises one or more repeat units according to Formula (I):

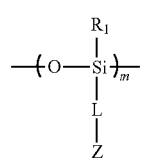

Formula (I)

wherein:
each $R_1$ is independently selected from the group consisting of H, OH, $C_1$-$C_{32}$ alkyl, $C_1$-$C_{32}$ substituted alkyl, $C_6$-$C_{32}$ aryl, $C_5$-$C_{32}$ substituted aryl, $C_6$-$C_{32}$ alkylaryl, C6-$C_{32}$ substituted alkylaryl, $C_1$-$C_{32}$ alkoxy and $C_1$-$C_{32}$ substituted alkoxy; preferably each $R_1$ is independently selected from the group consisting of H, OH, $C_1$-$C_{16}$ alkyl, $C_1$-$C_4$ alkoxy, more preferably each $R_1$ is independently selected from the group consisting of H, OH, methyl, methoxy, and ethoxy;

each L is a linking bivalent alkylene radical, preferably each L is independently selected from the group consisting of —$(CH_2)_s$—; —$(H_2C)_sOC_6H_4$—;

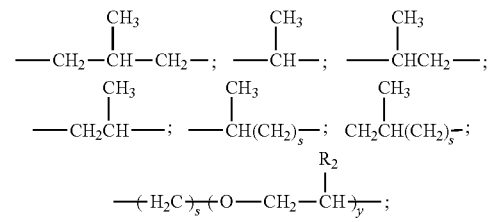

and combinations thereof;
wherein each $R_2$ is independently selected from the group consisting of H, $C_1$-$C_4$ alkyl, substituted alkyl, aryl, substituted aryl, and combinations thereof, preferably H or $C_1$-$C_4$ alkyl, most preferably H or methyl;

each s is independently an integer of from 1 to about 20, preferably each s is independently an integer of from 2 to about 12;

each y is independently an integer of from 1 to about 100, preferably each y is independently an integer of from 1 to about 20, more preferably y is independently an integer of from 1 to about 10;

each Z is independently selected from the group consisting of:

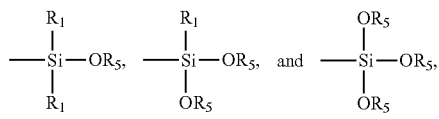

and
wherein each $R_1$, if present, is independently selected from the group as provided above, and
wherein each $R_5$ is independently selected from the group consisting of H, $C_1$-$C_{32}$ alkyl, $C_1$-$C_{32}$ substituted alkyl, $C_6$-$C_{32}$ aryl, $C_5$-$C_{32}$ substituted aryl, $C_6$-$C_{32}$ alkylaryl, and $C_6$-$C_{32}$ substituted alkylaryl, wherein at least one $R_5$ in the siloxane compound is formed from a hydroxyl-group-containing perfume raw material; and
wherein index m is an integer of from about 1 to about 500.

2. The consumer product composition according to claim 1, wherein L is —$(CH_2)_s$—.

3. The consumer product composition according to claim 1, wherein the siloxane compound further comprises one or more repeat units according to Formula (II):

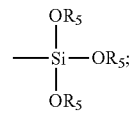

Formula (II)

wherein each $R_1$ is independently selected from the group as described above, and
wherein index p is an integer of from about 0 to about 500.

4. The consumer product composition according to claim 3, wherein the sum of index p+index m is from about 10 to about 1000.

5. The consumer product composition according to claim 3, wherein the ratio of p:m is from about 10:1 to about 1:5.

6. The consumer product composition according to claim 1, wherein the siloxane compound comprises one or more repeat units according to Formula (III), Formula (IV),

Formula (III)

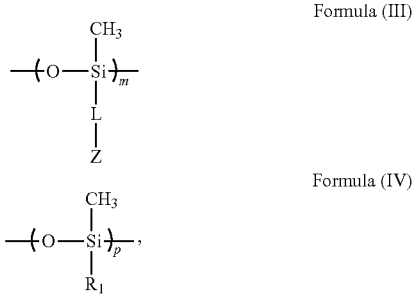

Formula (IV)

or mixtures thereof.

7. The consumer product composition according to claim 1, wherein $R_1$ is independently selected from C1-C32 alkyl groups.

8. The consumer product composition according to claim 1, wherein the siloxane compound comprises repeat units according to Formula (I), wherein at least one Z moiety is:

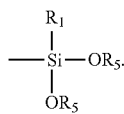

9. The consumer product composition according to claim 1, wherein the siloxane compound comprises repeat units according to Formula (I), wherein at least one Z moiety is $$-\underset{\underset{OR_5}{|}}{\overset{\overset{OR_5}{|}}{Si}}-OR_5;$$

wherein the carrier is a solid carrier,
wherein the carrier is a water-soluble carrier, and
wherein the carrier comprises polyalkylene glycol.

10. The consumer product composition according to claim 1, wherein the hydroxyl-group-containing perfume raw material comprises an aliphatic alcohol or aromatic alcohol.

11. The consumer product composition according to claim 1, wherein the hydroxyl-group-containing perfume raw material is selected from the group consisting of: farnesol; (1-Methyl-2-(1,2,2-trimethylbicyclo[3.1.0]-hex-3-ylmethyl) cyclopropyl)methanol; 2-Methyl-3-{(1,7,7-trimethylbicyclo{2.2.1}hept-2-yl)oxy}exo-1-propanol; 2-Methyl-4-(2,2,3-trimethylcyclopent-3-en-1-yl)butan-1-ol; ethyl trimethylcyclopentene butenol; 4-isopropylcyclohexanemethanol; 2-methyl-5-phenylpentan-1-ol; 3-methyl-5-phenylpentanol; 9-decenol; hindinol; cyclomethylene citronellol; 2,2-dimethyl-3-(3-methylphenyl)propan-1-01; citronellol; (2E,6Z)-nona-2,6-dien-1-ol; cedanol; isocyclogeraniol; geraniol; 3-phenylpropyl alcohol; cinnamic alcohol; trans-2-hexenol; 4-(5,5,6-trimethylbicyclo[2.2.1] hept-$2_1$)cyclohexan-1-ol; octalynol; ebanol; undecavertol; 4-penten-2-ol, 3,3-dimethyl-5-(2,2,3-trimethyl-3-cyclopenten-1-yl)-; 3-methyl-4-phenylbutan-2-ol; eugenol; 1-(2, 2,6-Trimethylcyclohexyl)hexan-3-ol; 5-propenyl-2-ethoxyphenol; 1-(4-isopropyl-cyclohexyl) ethanol; 2-pentylcyclopentanol; nerolidol; cedrol; hydroxycitronellal dimethyl acetal; florosa; 2,5,5-trimethyl-octahydronaphthalen-2-01; 2,5,5-trimethyl-1,2,3,4,4a,5,6,7-octahydro-2-naphthalenol; terpinen-4-ol; ethyl linalool; 1-methyl-3-(2-methylpropyl)cyclohexanol; 4-phenyl-2-methyl-2-butanol; 3,7-dimethyloctan-1,7-diol; 1-methyl-4-isopropylcyclohexane-8-ol; linalool; 3,7-dimethyl-4,6-octadien-3-ol; alpha terpineol; 2-methyl-1-phenylpropan-2-ol; cyclohexanepropanol,2,2-dimethyl-; dihydromyrcenol; tetrahydrolinalool; tetrahydro myrcenol; 2,6-dimethyl-2-heptanol; 2-hexen-1-ol; 3-hexen-1-ol; ethanol, 2,2'-oxybis-; methyl anthranilate; flor acetate; gamma hexalactone; para cresol; nerol oxide; hydratropic alcohol; dimethyl benzyl carbinol; dimethyl anthranilate; ethyl maltol; heptyl alcohol; ethanol, 2-(2-methoxyethoxy)-; cyclohexane ethanol; vanillin; ethyl vanillin; and mixtures thereof.

12. The consumer product composition according to claim 1, wherein the siloxane compound is formed from a parent silicone compound, wherein the viscosity of the parent silicone compound before attachment of the perfume raw material fragment is from about 10 cps to about 60,000cps.

13. The consumer product composition according to claim 1, wherein the composition comprises from about 0.1% to about 20%, by weight of the composition of the siloxane compound.

14. The consumer product composition according to claim 1, wherein the consumer product composition comprises at least about 50%, by weight of the composition, of water.

15. The consumer product composition according to claim 1, wherein the consumer product adjunct is selected from the group consisting of bleach activators, surfactants, delivery enhancing agents, builders, chelating agents, dye transfer inhibiting agents, dispersants, enzymes, enzyme stabilizers, catalytic metal complexes, polymeric dispersing agents, clay and soil removal/anti-redeposition agents, brighteners, suds suppressors, dyes, additional perfumes and/or perfume delivery systems, structure elasticizing agents, fabric conditioning actives (FCAs), anionic surfactant scavengers, carriers, hydrotropes, processing aids, structurants, anti-agglomeration agents, coatings, formaldehyde scavengers, deposition aids, emulsifiers, pigments, or mixtures thereof.

16. The consumer product composition according to claim 1, wherein the consumer product composition is in the form of a liquid composition, a granular composition, a single-compartment pouch, a multi-compartment pouch, a dissolvable sheet, a pastille or bead, a fibrous article, a tablet, a bar, a flake, a foam/mousse, a non-woven sheet, or a mixture thereof.

17. The consumer product composition according to claim 15, wherein the consumer product is in the form of a pastille or bead.

18. The consumer product composition according to claim 15, wherein the consumer product is in the form of a liquid composition.

19. The consumer product composition according to claim 1, wherein the consumer product further comprises a solid water-soluble carrier selected from the group consisting of water-soluble inorganic alkali metal salt, water-soluble alkaline earth metal salt, water-soluble organic alkali metal salt, water-soluble organic alkaline earth metal salt, water soluble carbohydrate, water-soluble silicate, water-soluble urea, and a combination thereof.

20. A method of treating a surface with the consumer product composition according to claim 1, comprising the step of contacting the surface with the consumer product composition, optionally in the presence of water.

* * * * *